US012685464B2

(12) United States Patent
Yang et al.

(10) Patent No.: US 12,685,464 B2
(45) Date of Patent: Jul. 21, 2026

(54) TRANSABDOMINAL FETAL OXIMETRY BASED ON FREQUENCY-MODULATED CONTINUOUS-WAVE NEAR-INFRARED SPECTROSCOPY

(71) Applicant: The Regents of the University of California, Oakland, CA (US)

(72) Inventors: Weijian Yang, Redwood, CA (US); Shing-Jiuan Liu, Davis, CA (US); Soheil Ghiasi, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 457 days.

(21) Appl. No.: 18/249,714

(22) PCT Filed: Nov. 24, 2021

(86) PCT No.: PCT/US2021/060875
§ 371 (c)(1),
(2) Date: Apr. 19, 2023

(87) PCT Pub. No.: WO2022/115643
PCT Pub. Date: Jun. 2, 2022

(65) Prior Publication Data
US 2024/0023846 A1 Jan. 25, 2024

Related U.S. Application Data

(60) Provisional application No. 63/118,359, filed on Nov. 25, 2020.

(51) Int. Cl.
A61B 5/1464 (2006.01)
A61B 5/00 (2006.01)
A61B 5/1455 (2006.01)

(52) U.S. Cl.
CPC ........ A61B 5/1464 (2013.01); A61B 5/14552 (2013.01); A61B 5/7203 (2013.01);
(Continued)

(58) Field of Classification Search
CPC . A61B 5/1464; A61B 5/14552; A61B 5/7203; A61B 5/7257; A61B 5/7267;
(Continued)

(56) References Cited

U.S. PATENT DOCUMENTS

2010/0152559 A1    6/2010  Cheng et al.
2013/0286379 A1*  10/2013  Li ........................ A61B 5/0095
                                                                      356/40
(Continued)

FOREIGN PATENT DOCUMENTS

WO       WO-2019204231 A1 * 10/2019  ........... A61B 5/4064

OTHER PUBLICATIONS

Ayres-de-Campos, D., et al., "FIGO Consensus Guidelines on Intrapartum Fetal Monitoring: Cardiotocography", In International Journal of Gynecology and Obstetrics, vol. 131, Oct. 2015, pp. 13-24.
(Continued)

*Primary Examiner* — Abid A Mustansir
(74) *Attorney, Agent, or Firm* — Byrne Poh LLP

(57) ABSTRACT

This disclosure provides transabdominal fetal oximetry (TFO) that uses frequency-modulated continuous-wave (FMCW) time-domain near-infrared spectroscopy to measure time-resolved reflectance values of light signals collected from a maternal-fetal multilayer tissue structure. In
(Continued)

TRANSABDOMINAL FETAL OXIMETRY (TFO) SYSTEM 100 various embodiments, the disclosed FMCW time-domain near-infrared spectroscopy is configured to function as an optical interferometer that uses two frequency-swept laser sources of different center wavelengths λ1 and λ2 as probe lights to detect optical property in vascular tissues of the maternal-fetal multilayer tissue structure. The FMCW near-infrared spectroscopy is configured to collect light signals returned from the multilayer structure and generate a time-resolved reflectance curve based on the collected light signals.

31 Claims, 12 Drawing Sheets

(52) U.S. Cl.
CPC .......... *A61B 5/7257* (2013.01); *A61B 5/7267* (2013.01); *A61B 2562/0233* (2013.01)

(58) Field of Classification Search
CPC ........ A61B 2562/0233; A61B 2503/02; A61B 5/0075; A61B 5/6823; A61B 5/4362
See application file for complete search history.

(56) References Cited

U.S. PATENT DOCUMENTS

| | | |
|---|---|---|
| 2020/0214603 A1 | 7/2020 | Ghiasi et al. |
| 2020/0245879 A1 | 8/2020 | Ghiasi et al. |
| 2020/0271515 A1 | 8/2020 | Roulston et al. |
| 2020/0323467 A1* | 10/2020 | Ray ..................... A61B 5/0075 |

OTHER PUBLICATIONS

Devane, D., et al., "Cardiotocography versus Intermittent Auscultation of Fetal Heart on Admission to Labour Ward for Assessment of Fetal Wellbeing", In Cochrane Database of Systematic Reviews, vol. 2, Feb. 2012, pp. 1-35.

East, C.E. et al., "Fetal Pulse Oximetry for Fetal Assessmetn in Labour", In Cochrane Databse Systematic Reviews, vol. 2, Apr. 2007, pp. 1-57.

East, C.E., et al., "Update on Intrapartum Fetal Pulse Oximetry", In Aust. N.Z.J. Obstet. Gynaecol. vol. 42, No. 1, Feb. 2002, pp. 119-124.

Fong, D.D., eta l., "Design and In Vivo Evaluation of a Non-invasive Transabdominal Fetal Pulse Oximeter", In IEEE Transactions on Biomedical Engineering, Jun. 2020, pp. 1-9.

* cited by examiner

TRANSABDOMINAL FETAL OXIMETRY (TFO) SYSTEM 100

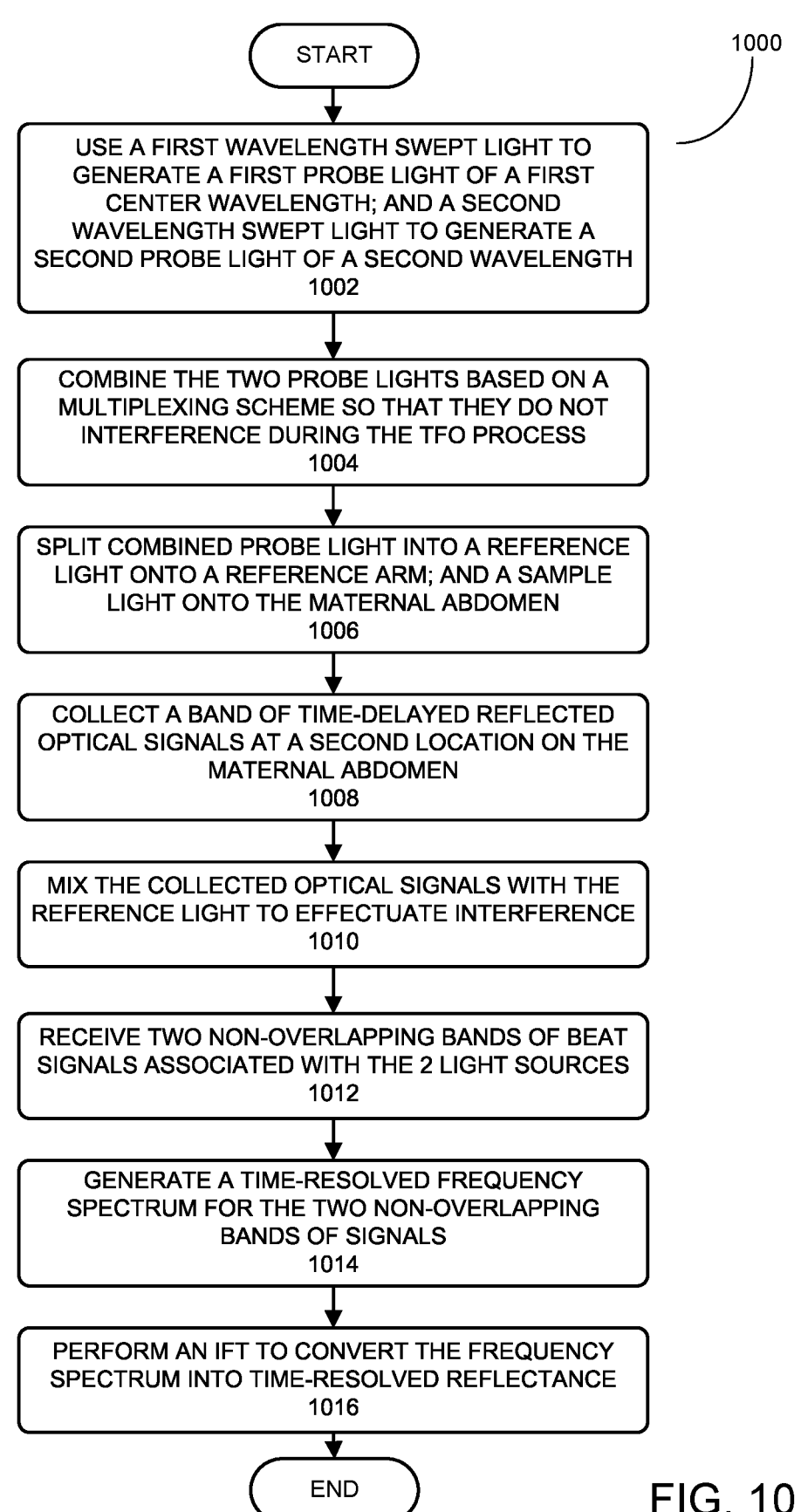

START

USE A FIRST WAVELENGTH SWEPT LIGHT TO GENERATE A FIRST PROBE LIGHT OF A FIRST CENTER WAVELENGTH; AND A SECOND WAVELENGTH SWEPT LIGHT TO GENERATE A SECOND PROBE LIGHT OF A SECOND WAVELENGTH
1002

COMBINE THE TWO PROBE LIGHTS BASED ON A MULTIPLEXING SCHEME SO THAT THEY DO NOT INTERFERENCE DURING THE TFO PROCESS
1004

SPLIT COMBINED PROBE LIGHT INTO A REFERENCE LIGHT ONTO A REFERENCE ARM; AND A SAMPLE LIGHT ONTO THE MATERNAL ABDOMEN
1006

COLLECT A BAND OF TIME-DELAYED REFLECTED OPTICAL SIGNALS AT A SECOND LOCATION ON THE MATERNAL ABDOMEN
1008

MIX THE COLLECTED OPTICAL SIGNALS WITH THE REFERENCE LIGHT TO EFFECTUATE INTERFERENCE
1010

RECEIVE TWO NON-OVERLAPPING BANDS OF BEAT SIGNALS ASSOCIATED WITH THE 2 LIGHT SOURCES
1012

GENERATE A TIME-RESOLVED FREQUENCY SPECTRUM FOR THE TWO NON-OVERLAPPING BANDS OF SIGNALS
1014

PERFORM AN IFT TO CONVERT THE FREQUENCY SPECTRUM INTO TIME-RESOLVED REFLECTANCE
1016

END

COMBINED TIME-RESOLVED REFLECTANCE CURVE 1100

MATERNAL SIGNALS
1102

MATERNAL-FETAL MIXED
SIGNALS
1104

TRANSABDOMINAL FETAL OXIMETRY BASED ON FREQUENCY-MODULATED CONTINUOUS-WAVE NEAR-INFRARED SPECTROSCOPY

CROSS-REFERENCE TO RELATED APPLICATION

This application claims the benefit of U.S. Provisional Patent Application Ser. No. 63/118,359, entitled "Transabdominal Fetal Oximetry Through Time-Domain Near-infrared Spectroscopy," filed on 25 Nov. 2020, the contents of which are incorporated by reference herein.

GOVERNMENT LICENSE RIGHTS

This invention was made with U.S. government support under grant number 1838939 awarded by the National Science Foundation (NSF). The U.S. government has certain rights in the invention.

BACKGROUND

Field

The disclosed embodiments generally relate to non-invasive techniques for monitoring the health of a fetus in utero. More specifically, the disclosed embodiments relate to a technique for performing robust, clinical-grade transabdominal fetal pulse oximetry.

Related Art

Assessing fetal well-being during labor is an important indicator of whether caesarean section (C-section) or instrumental vaginal delivery is needed. During assessment, one critical parameter to evaluate fetal well-being is the oxygen saturation level of the fetus. Transabdominal fetal oximetry has great significance in medical care in obstetrics. It can non-invasively measure the blood oxygen saturation in fetus through the maternal abdomen, and provide an important assessment to intrapartum fetal health and early detection of fetal hypoxia.

One existing technique, referred to as the "continuous-wave" (CW) technique is based on using fetal pulse oximetry. Generally speaking, with this technique pulse oximetry can measure the arterial oxygen saturation using a CW laser. More specifically, a light source with constant wavelength (near infrared) and constant intensity is shined through maternal tissue and onto a fetus. Arterial pulsations from the maternal and fetal heartbeats cause small changes in the tissue's light absorption, which results in changes in intensity of the diffused-reflected light measured at the surface of maternal abdomen. By measuring this change in the diffused-reflected light signal, the oxygen saturation of the fetus can be extracted. Note that the CW technique is non-invasive as both the probe and the sensor(s) are placed on the maternal abdomen. However, in the CW technique the diffuse-reflected light from the fetus is often mixed with the diffuse-reflected light from the maternal tissues. The complication in separating the maternal signals from the fetal signals often leads to degradation in accuracy of the CW-based fetal pulse oximetry.

Hence, what is needed is a more accurate technique for measuring fetal blood oxygenation without the drawbacks of existing techniques.

SUMMARY

This disclosure provides transabdominal fetal oximetry (TFO) technique that uses a disclosed frequency-modulated continuous-wave (FMCW) time-domain near-infrared spectroscopy to measure time-resolved reflectance of light collected from a maternal-fetal multilayer tissue structure. In various embodiments, the disclosed FMCW near-infrared spectroscopy is configured to function as an optical interferometer that uses two frequency-swept laser sources of different central wavelengths $\lambda_1$ and $\lambda_2$ as probe lights to detect optical property changes in vascular tissues of the maternal-fetal multilayer tissue structure. The disclosed FMCW near-infrared spectroscopy is further configured to collect light signals returned from the multilayer structure and generate a time-resolved reflectance curve based on the collected light signals.

More specifically, the disclosed TFO estimates maternal/fetal oxygen saturation levels in two phases: (1) a measurement phase and (2) a data processing phase. During the measurement phase, the disclosed FMCW near-infrared spectroscopy uses two frequency-swept laser sources of different central wavelengths $\lambda_1$ and $\lambda_2$ as probe lights to shine on the maternal abdomen. The probe lights penetrate through both a maternal tissue layer and an underlining fetal tissue layer, and the diffused/scattered and reflected lights (collectively referred to as "returned lights" or "returned light signals" hereinafter) reemerge at the maternal abdomen surface. The returned light signals of the probe lights are collected and combined with reference lights from a reference arm of the disclosed FMCW near-infrared spectroscopy, which causes interference between the returned light signals and the reference lights. The interference processes generate a range of beat signals which are separated in the time-domain, and from which time-of-flight (TOF) (also referred to as "time-resolved" hereinafter) reflectance values associated with the returned lights are extracted and a time-resolve reflectance curve for the returned lights having different path-lengths is generated. This concludes the measurement phase of the disclosed FMCW near-infrared spectroscopy, and then the data processing phase begins.

In different embodiments, various light multiplexing/demultiplexing techniques are used in the disclosed FMCW near-infrared spectroscopy to combine the two laser lights prior to probing the tissues and to optionally divide the generated beat signals into two groups based on the two different wavelengths $\lambda_1$ and $\lambda_2$. As a result, the beat signals belonging to different light sources can be easily separately and distinguished during the data processing phase of the TFO process.

During the data processing phase, the experimental time-resolve reflectance curve is fitted to a diffusion-approximated reflectance curve generated by a multilayer tissue model derived from diffusion equations, e.g., by using nonlinear fitting through an iterative optimization process. As an alternative to model fitting, a data-driven machine learning technique can be used to first build a neural network model off-line that can predict optical absorption coefficients, optical scattering coefficients and the layer thicknesses in a multi-layer structure. The trained machine-learning model is then used online during real-time oxygen saturation measurements by receiving the experimental time-resolved reflectance curves and outputting real-time estimated optical absorption coefficients and optical scattering coefficients for each layer in maternal-fetal multilayer tissue structure at each wavelength $\lambda_1$ and $\lambda_2$. Finally, oxygen saturation levels for the mother and fetus can be estimated based on Eqns. (1) and (4) in this patent disclosure using the extracted optical coefficients. This concludes the data processing phase of the disclosed TFO procedure.

Note that by using two probe lights of different central wavelengths and by sweeping the two wavelengths in the time-domain, the disclosed TFO procedure allows absolute values of the optical properties of the maternal-fetal multilayer tissue structure and the absolute concentrations of the oxygenated hemoglobin and deoxygenated hemoglobin to be extracted, and thus the oxygen saturation levels for both mother and fetus can be computed based on Eqn. (1). Moreover, by sweeping the probing wavelengths and setting up the interferometer operation, the disclosed FMCW near-infrared spectroscopy allows different scattered-reflected light paths of different path lengths to be resolved/separated in the time-domain, and visualized using the time-resolved reflectance curve. The ability to resolve in the time-domain a group of light paths having different path lengths in the multilayer structure does not exist in conventional continuous-wave (CW) transabdominal fetal pulse oximetry systems.

Hence, the disclosed TFO and FMCW spectroscopy provide a noninvasive, highly accurate, real-time, and cost-effective fetal oxygen saturation measurement procedure and system, which is expected to play an important role in monitoring intrapartum fetal health.

In one aspect, a frequency-modulated continuous-wave (FMCW) process for non-invasively measuring a fetal blood oxygenation level is disclosed. This process begins by receiving a first frequency-modulated light source having a central wavelength of $\lambda_1$ as a first probe light; and simultaneously receiving a second frequency-modulated laser source having a central wavelength of $\lambda_2$ as a second probe light. The process then splits the first probe light into a first reference light and a first sample light and the second probe light into a second reference light and a second sample light. Next, the process uses the first probe light and the second probe light to probe a maternal-fetal multilayer tissue structure, thereby generating a first band of light signals and a second band of light signals carrying information of the maternal-fetal multilayer tissue structure. Next, the process mixes the first and second reference lights with the first and second bands of light signals, respectively to effectuate interferences between the first or the second reference light and the first or second band of light signals to produce a band of beat frequencies. The process subsequently generates a time-resolved reflectance curve based on the band of beat frequencies. The process next determines a set of optical properties for the fetus in the maternal-fetal multilayer tissue structure for both central wavelengths $\lambda_1$ and $\lambda_2$. The process finally performs a pulse-oximetry computation based on the determined optical properties to determine a fetal oxygen saturation level.

In some embodiments, each of the first and second reference light propagates a known distance toward a coupler while each of the first and second sample lights propagates a first distance to incident on a maternal abdomen of the maternal-fetal multilayer tissue structure. Each of the sample lights then traverses through the maternal abdomen and is scattered inside the fetus into the first or the second band of light signals of a range of optical path lengths. The first and second bands of light signals propagate back onto a surface of the maternal abdomen and collected by one or more detectors.

In some embodiments, a time-resolution of the time-resolved reflectance curve is increased by increasing a frequency-sweeping range of the first and the second frequency-modulated light sources.

In some embodiments, the generated time-resolved reflectance curve is composed of two portions: a first portion of the time-resolved reflectance curve corresponding to the first probe light with central wavelengths $\lambda_1$; and a second portion of the time-resolved reflectance curve corresponding to the second probe light with central wavelengths $\lambda_2$.

In some embodiments, the wavelengths/frequencies of the first and the second frequency-modulated light sources are continuously and periodically modulated based on a wavelength/frequency modulation waveform.

In some embodiments, the wavelength/frequency modulation waveform is either a linear waveform or a nonlinear waveform.

In some embodiments, the maximum range of wavelength modulation of the first and the second frequency-modulated light sources is significantly smaller than the difference between $\lambda_1$ and $\lambda_2$.

In some embodiments, the each of the first and second band of light signals propagates a second distance from the one or more detectors toward a coupler. Note that the sum of the first distance and the second distance is substantially equal to the known distance.

In some embodiments, the process generates the time-resolved reflectance curve based on the band of beat frequencies by: generating a beat spectrum based on the band of beat frequencies and a corresponding set of intensity values of the band of beat frequencies; and obtaining the time-resolved reflectance curve by performing an inverse Fourier Transformation (iFT) on the beat spectrum.

In some embodiments, each data point on the time-resolved reflectance curve specifies both a reflectance value and a time-delay of a given light signal in either the first or the second band of light signals.

In some embodiments, the time-resolved reflectance curve has a bell-shaped distribution.

In some embodiments, the time-resolved reflectance curve includes two non-overlapping bell-shaped distributions which correspond to the first probe light and the second probe light, respectively.

In some embodiments, the time-resolved reflectance curve is regenerated for each frequency modulation period of the first probe light and the second probe light. Moreover, each regenerated time-resolved reflectance curve is used to determine a new value of the fetal oxygen saturation level.

In some embodiments, the set of optical properties includes at least: $\mu_{a,\lambda 1}$: a first optical absorption coefficient of fetal tissues in the maternal-fetal multilayer tissue structure corresponding to wavelengths $\lambda_1$; and $\mu_{a,\lambda 2}$: a second optical absorption coefficient of the fetal tissues in the maternal-fetal multilayer tissue structure corresponding to wavelengths $\lambda_2$.

In some embodiments, the process performs the oximetry computation based on the determined optical properties to determine a fetal oxygen saturation level by: extracting absolute concentrations of the oxygenated hemoglobin ([HbO$_2$]) and deoxygenated hemoglobin ([Hb]) associated with the fetal tissues using $\mu_{a,\lambda 1}$ and $\mu_{a,\lambda 2}$; and determining a new fetal oxygen saturation level by computing [HbO$_2$]/([HbO$_2$]+[Hb])×100%.

In some embodiments, the set of optical properties additionally includes: a first optical reduced scattering coefficient of the fetal tissues corresponding to wavelengths $\lambda_1$; and a second optical reduced scattering coefficient of the fetal tissues corresponding to wavelengths $\lambda_2$.

In some embodiments, the process determines the set of optical properties for the fetus by fitting the time-resolved reflectance curve to a multilayer tissue model for the maternal-fetal multilayer tissue structure. Note that fitting the time-resolved reflectance curve to the tissue model additionally produces absorption coefficients and/or reduced scattering coefficients for maternal tissues in the maternal-fetal multilayer tissue structure. Moreover, the oximetry computation additionally determines a maternal blood oxygenation level.

In some embodiments, the process collects the first and second bands of light signals from the surface of the maternal abdomen comprises using one of the following: a fiber-based coupling technique; a free-space-based coupling technique; and a hybrid fiber-based and free-space-based coupling technique.

In some embodiments, prior to splitting each of the first probe light and the second probe light into a reference light and a sample light, the process further performs a multiplexing operation on the first probe light and the second probe light to combine the two probe lights by using one of the following techniques: time-division multiplexing; frequency-division multiplexing; and radio-frequency-division multiplexing.

In some embodiments, the process determines the set of optical properties based on the generated time-resolved reflectance curve by first receiving a training neural network model which was trained based on a simulated time-resolved reflectance curve generated by a multilayer model that simulates the maternal-fetal multilayer tissue structure. The process then uses the generated time-resolved reflectance as input to the trained neural network model, wherein the trained neural network model outputs estimated optical properties of the maternal-fetal multilayer tissue structure.

In some embodiments, the process further includes using more than two probe lights to measure the fetal blood oxygenation level. For example, the process can add a third frequency-modulated light source to generate a third probe light having a central wavelength of $\lambda_3$. Next, the process applies the same processing steps of claim 1 on the third probe light while concurrently applying the same processing steps on the first and second probe light. By adding one or more additional probe lights in the FMCW-based fetal blood oxygenation level measurements, the process can increase measurement accuracies.

In another aspect, a frequency-modulated continuous-wave (FMCW) time-domain near-infrared spectroscopy for non-invasively measuring a fetal blood oxygenation level is disclosed. The FMCW time-domain near-infrared spectroscopy includes: (1) a first frequency-modulated light source to generate a first probe light having a central wavelength of $\lambda_1$ and a second frequency-modulated laser source to generate a second probe light having a central wavelength of $\lambda_2$; (2) an interferometer configured to determine a time-resolved reflectance curve for each of the first probe light and the second probe light during a fetal oximetry, this interferometer further includes: (2a) splitter configured to split the first probe light into a first reference light and a first sample light and the second probe light into a second reference light and a second sample light; (2b) a guiding mechanism configured to guide the first probe light and the second probe light to probe a maternal-fetal multilayer tissue structure, thereby generating a first band of light signals and a second band of light signals carrying information of the maternal-fetal multilayer tissue structure; and (2c) a coupler configured to receive and mix the first and second reference lights with the first and second bands of light signals, respectively to effectuate an interference between the first or the second reference light and the first or second band of light signals to produce a band of beat frequencies. The FMCW time-domain near-infrared spectroscopy further includes a processing for generating a time-resolved reflectance curve based on the band of beat frequencies.

In some embodiments, the guiding mechanism further includes: (1) a reference arm having a known distance and configured to guide the first and the second reference lights toward the coupler, and (2) a sample arm configured to guide the first and second sample lights to incident on a maternal abdomen of the maternal-fetal multilayer tissue structure, wherein each of the sample lights traverses through the maternal abdomen and is scattered inside the fetus into the first or the second band of light signals of a range of optical path lengths, and wherein the first and second bands of light signals propagate back onto a surface of the maternal abdomen and collected by one or more detectors In some embodiments, the one or more detectors are configured to couple the first and second bands of light signals from the surface of the maternal abdomen to the coupler through a second distance, wherein the sum of the first distance and the second distance is substantially equal to the known distance.

In some embodiments, the FMCW time-domain near-infrared spectroscopy further includes a wavelength/frequency modulation module configured to continuously and periodically modulate the first probe light and the second probe light based on a wavelength/frequency modulation waveform.

In some embodiments, the processing unit is configured to generate a time-resolved reflectance curve by: generating a beat spectrum based on the band of beat frequencies and a corresponding set of intensity values of the band of beat frequencies; and obtaining the time-resolved reflectance curve by performing an inverse Fourier Transformation (iFT) on the beat spectrum.

In some embodiments, the processing unit is further configured to regenerate a new time-resolved reflectance curve for each frequency modulation period of the first probe light and the second probe light. Note that each regenerated time-resolved reflectance curve is used to determine a new value for the fetal oxygen saturation level.

In some embodiments, the processing unit is further configured to: (1) determine a set of optical properties for the fetus in the maternal-fetal multilayer tissue structure for both central wavelengths $\lambda_1$ and $\lambda_2$ by fitting the time-resolved reflectance curve to a multilayer tissue model for maternal tissues and fetal tissues; and (2) perform an oximetry computation based on the determined optical properties to determine the a fetal oxygen saturation level.

In some embodiments, the FMCW time-domain near-infrared spectroscopy further includes a multiplexer (MUX) positioned before the splitter and configured to perform a multiplexing operation on the first probe light and the second probe light to combine the two probe lights by using one of the following techniques: time-division multiplexing; frequency-division multiplexing; and radio-frequency-division multiplexing.

In some embodiments, the FMCW time-domain near-infrared spectroscopy further includes a third frequency-modulated light source to generate a third probe light having a central wavelength of $\lambda_3$; and the interferometer is further configured to determine the time-resolved reflectance curve for the third probe light during the fetal pulse-oximetry.

In yet another aspect, a FMCW method for non-invasively measuring a fetal blood oxygenation level includes the steps of: using a first wavelength swept laser source to generate light having a central wavelength $\lambda_1$; using a second wavelength swept laser source to generate light having a central wavelength $\lambda_2$; using an interferometer to determine a time-resolved reflectance for each of the two central wavelengths $\lambda_1$ and $\lambda_2$ by: (1) splitting light from the first and second swept laser sources between a reference arm that has a known distance, and a sample arm that directs light into a maternal abdomen of a pregnant mammal toward a fetus, and returns reflected light that is coupled from different detection locations on the maternal abdomen; (2) combining light from the reference and sample arms to produce time-domain interference fringe patterns; calculating the time-resolved reflectances based on the time-domain interference fringe patterns; determining absorption coefficients and/or reduced scattering coefficients for the fetal tissue for both central wavelengths $\lambda_1$ and $\lambda_2$ by fitting the time-resolved reflectances to a tissue model for maternal tissue and fetal tissue based on known source-to-detector distances; and performing a pulse-oximetry computation based on the determined absorption coefficients to determine the fetal blood oxygenation level.

In still another aspect, a combined frequency-modulated continuous-wave (FMCW) and continuous wave (CW) process for non-invasively measuring a fetal blood oxygenation level includes the steps of: (1) using a CW method, which directs light from two or more light sources into a maternal abdomen toward a fetus and receives reflected light from different locations on the maternal abdomen, to produce received signals, and performs a filtering operations on the received signals in the time domain to produce fetal signals, which are used to determine a first fetal blood oxygenation level; (2) using a FMCW method that uses an interferometer, which splits light from two or more laser sources between a reference arm and a sample arm, wherein the sample arm directs light into a maternal abdomen of a pregnant mammal toward a fetus and returns reflected light coupled from different detection locations on the maternal abdomen, and wherein the interferometer combines light from the reference and sample arms to produce interference patterns, which are used to determine a second fetal blood oxygenation level; and (3) determining a composite fetal blood oxygenation level based on the first and second fetal blood oxygenation levels.

In some embodiments, the combined FMCW and CW process further includes the steps of: (1) using the FMCW method to determine a path-length parameter; and (2) using the CW method, which directs light from two or more light sources into a maternal abdomen toward a fetus and receives reflected light from different locations on the maternal abdomen, to produce received signals, and performs a filtering operations on the received signals in the time domain based on the determined path-length parameter to produce fetal signals, which are used to determine the fetal blood oxygenation level.

BRIEF DESCRIPTION OF THE FIGURES

FIG. 10 presents a flowchart illustrating a process performed by the disclosed FMCW near-infrared spectroscopy to generate a time-resolved reflectance curve from the collected optical signals having different time delays in accordance with the disclosed embodiments.

DETAILED DESCRIPTION

Figure 1:
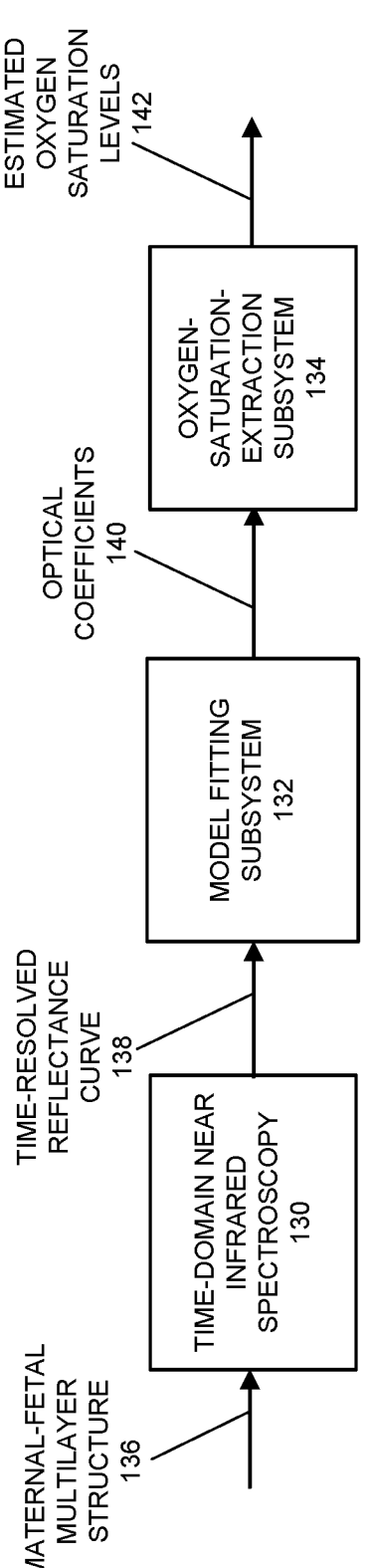
FIG. 1 shows a schematic diagram illustrating a transabdominal fetal oximetry system using the disclosed frequency-modulated continuous-wave (FMCW) near-infrared spectroscopy, and the corresponding data processing subsystems for performing transabdominal fetal oximetry in accordance with the disclosed embodiments.

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Terminology

Throughout this disclosure, the terms "time-of-flight" or "TOF" and "time delay" are used interchangeably to mean an optical path-length traversed by a given optical signal in a maternal-fetal multiplayer tissue structure before being detected in the disclosed FMCW near-infrared spectroscopy. Moreover, the term "frequency-modulation" and "wavelength-modulation" are used interchangeably to mean the action of continuously and periodically modulating a light source in preparation for the FMCW-based TFO measurements.

Overview

This disclosure provides transabdominal fetal oximetry (TFO) that uses FMCW near-infrared spectroscopy to measure time-resolved reflectance of light collected from a maternal-fetal multilayer tissue structure. In various embodiments, the disclosed FMCW near-infrared spectroscopy is configured to function as an optical interferometer that uses two frequency-swept laser sources of different center wavelengths $\Delta_1$ and $\Delta_2$ as probe lights to detect optical property changes in vascular tissues of the maternal-fetal multilayer tissue structure. The FMCW near-infrared spectroscopy is configured to collect light signals returned from the multilayer structure and generate a time-resolved reflectance curve based on the collected light signals.

More specifically, the disclosed TFO estimates maternal/fetal oxygen saturation levels in two phases: (1) a measurement phase; and (2) a data processing phase. During the measurement phase, the disclosed FMCW near-infrared spectroscopy uses two frequency-swept laser sources of different central wavelengths $\lambda_1$ and $\lambda_2$ as probe lights to shine on the maternal abdomen. The probe lights penetrate through both a maternal tissue layer and an underlining fetal tissue layer, and the diffused/scattered and reflected lights (collectively referred to as "returned lights" or "returned light signals" hereinafter) reemerge at the maternal abdomen surface. The returned light signals of the probe lights are collected and combined with reference lights from a reference arm of the disclosed FMCW near-infrared spectroscopy, which causes interference between the returned light signals and the reference lights. The interference processes generate a range of beat signals which are separated in the time-domain, and from which time-of-flight (TOF) (also referred to as "time-resolved" hereinafter) reflectance values associated with the returned lights are extracted and a time-resolve reflectance curve for the returned lights having different path-lengths is generated. This concludes the measurement phase of the disclosed FMCW near-infrared spectroscopy, and then the data processing phase begins.

In different embodiments, various light multiplexing/demultiplexing techniques are used in the disclosed FMCW near-infrared spectroscopy to combine the two laser lights prior to probing the tissues and to optionally divide the generated beat signals into two groups based on the two different wavelengths $\lambda_1$ and $\lambda_2$. As a result, the beat signals belonging to different light sources can be easily separately and distinguished during the data processing phase of the TFO process.

During the data processing phase, the experimental time-resolve reflectance curve is fitted to a diffusion-approximated reflectance curve generated by a multilayer tissue model derived from diffusion equations, e.g., by using nonlinear fitting through an iterative optimization process. As an alternative to model fitting, a data-driven machine learning technique can be used to first build a neural network model off-line that can predict optical absorption coefficients, optical scattering coefficients and the layer thicknesses in a multi-layer structure. The trained machine-learning model is then used online during real-time oxygen saturation measurements by receiving the experimental time-resolved reflectance curves and outputting real-time estimated optical absorption coefficients and optical scattering coefficients for each layer in maternal-fetal multilayer tissue structure at each wavelength $\lambda_1$ and $\lambda_2$. Finally, oxygen saturation levels for the mother and fetus can be estimated based on Eqns. (1) and (4) in this patent disclosure using the extracted optical coefficients. This concludes the data processing phase of the disclosed TFO procedure.

Note that by using two probe lights of different central wavelengths and by sweeping the two wavelengths in the time-domain, the disclosed TFO procedure allows absolute values of the optical properties of the maternal-fetal multilayer tissue structure, and the absolute concentrations of the oxygenated hemoglobin and deoxygenated hemoglobin to be extracted and thus the oxygen saturation levels for both mother and fetus can be computed based on Eqn. (1). Moreover, by sweeping the probing wavelengths and setting up the interferometer operation, the disclosed FMCW near-infrared spectroscopy allows different scattered-reflected light paths of different path lengths to be resolved/separated in the time-domain, and visualized using the time-resolved reflectance curve. The ability to resolve in the time-domain a group of light paths having different path lengths in the multilayer structure does not exist in conventional continuous-wave (CW) transabdominal fetal pulse oximetry systems.

Hence, the disclosed TFO and FMCW spectroscopy provide a noninvasive, highly accurate, real-time, and cost-effective fetal oxygen saturation measurement procedure and system, which is expected to play an important role in monitoring intrapartum fetal health.

Continuous-Wave (CW) Transabdominal Fetal Pulse Oximetry

CW transabdominal fetal pulse oximetry is a fully noninvasive technique to measure fetal oxygen saturation level in real time. During a CW transabdominal fetal pulse oximetry measurement, two wavelengths of near-infrared lights emitted at constant frequencies and amplitudes are shone through the maternal abdomen, propagating through the maternal tissues to reach the underlying fetal vascular tissues, such as a fetal artery. During one heartbeat cycle of the fetus, there is a small variation of the blood volume in the artery, leading to a change of the light absorption mainly due to the concentration change of two chromophores: oxyhemoglobin ($HbO_2$) and deoxyhemoglobin (Hb). The arterial oxygen saturation $S_pO_2$ for pulse oximetry is defined as:

$$Sp\,O_2 = \frac{[Hb\,O_2]}{[Hb\,O_2 - [Hb]} \times 100\%^{15} \tag{1}$$

When two wavelengths $\lambda_1$ and $\lambda_2$ are used, oxygen saturation $S_pO_2$ can be rewritten in term of a modulation ratio R that is the ratio between the changes in light attenuation $\Delta A$ of the two wavelengths: $\Delta A_{\lambda 1}/\Delta A_{\lambda 2}$, wherein $\Delta A_{\lambda 1}$ and $\Delta A_{\lambda 2}$ are functions of $\langle L \rangle_{\lambda 1}$ and $\langle L \rangle_{\lambda 2}$, i.e., the expected photon path-lengths that light A or $\lambda_2$ traverse through the tissue from the point of incident on the tissue to the point of existing the tissue. Moreover, each expected photon path-length $\langle L \rangle_{\lambda}=L\times B_{\lambda}$, where L is the source-detector distance and $B_{\lambda}$ is the path-length factor at wavelength $\lambda$, which is related to the tissue scattering. Hence, $S_pO_2$ can be further rewritten as a function of the ratio of the two path-length factors $B_{\lambda 1}/B_{\lambda 2}$.

In conventional techniques, $B_{\lambda 1}/B_{\lambda 2}$ is often assumed or approximated to be 1, so that $S_pO_2$ is reduced to be merely a function of the modulation ratio R without $B_{\lambda 1}/B_{\lambda 2}$. Modulation ratio R is then experimentally determined and the value of $S_pO_2$ is subsequently obtained. Hence, in two-wavelength CW transabdominal fetal pulse oximetry, the fetal oxygen saturation is derived from the measurement of the changes in optical density caused by arterial pulsations at the two different wavelengths. However, the assumption that the ratio of expected photon path-length R at different wavelengths can be empirically determined in pulse oximetry can cause imprecise or sometimes inaccurate calculation/extraction of $S_pO_2$.

Based on the above discussion, two observations can be made. Firstly, if we can directly determine the absolute concentrations of the oxygenated hemoglobin ($HbO_2$) and deoxygenated hemoglobin (Hb) for mother and fetus, then the mother and fetus oxygen saturation levels are easily determined. Secondly, even if we could not directly determine $HbO_2$ and Hb, but we can accurately measure the expected photon path-lengths $\langle L \rangle_{\lambda 1}$ and $\langle L \rangle_{\lambda 2}$, or the ratio of the two expected photon path-lengths $\langle L \rangle_{\lambda 1}/\langle L \rangle_{\lambda 2}$, (or equivalently, the ratio of two path-length factors $B_{\lambda 1}/B_{\lambda 2}$), then arterial oxygen saturation levels $S_pO_2$ for both mother and fetus can be more accurately determined than the conventional two-wavelength CW transabdominal fetal pulse techniques described above.

Transabdominal Fetal Oximetry (TFO) Through Time-Domain Near-Infrared Spectroscopy FIG. 1 shows a schematic diagram illustrating a disclosed transabdominal fetal oximetry system 100 including the disclosed FMCW near-infrared spectroscopy 130 and the corresponding data processing subsystems for performing transabdominal fetal oximetry in accordance with the disclosed embodiments. As can be seen in FIG. 1, transabdominal fetal oximetry system 100 includes FMCW near-infrared spectroscopy 130, which is followed by model fitting subsystem 132, which is further followed by oxygen-saturation-extraction subsystem 134.

Note that FMCW near-infrared spectroscopy 130 can receive a maternal-fetal multilayer structure 136. FMCW near-infrared spectroscopy 130 is configured to measure time-resolved reflectance of light signals collected from maternal-fetal multilayer tissue structure 136 (or simply "multilayer structure 316"). In some embodiments, the disclosed FMCW near-infrared spectroscopy 130 is configured to function as an optical interferometer that uses two frequency-swept laser sources of different center wavelengths $\lambda_1$ and $\lambda_2$ as probe lights to detect optical property changes in vascular tissues of maternal-fetal multilayer structure 136. FMCW near-infrared spectroscopy 130 is further configured to collect light signals reemerged from multilayer structure 136, and generate a time-resolved reflectance curve 138 based on the collected light signals.

As can be seen in FIG. 1, model fitting subsystem 132 receives time-resolved reflectance curve 138 as input. Model fitting subsystem 132 is configured to fit time-resolved reflectance curve 138 to a diffusion-approximated reflectance curve generated by a multilayer tissue model derived from diffusion models using an iterative optimization process, wherein the optical absorption coefficients and optical scattering coefficients are some of the fitting parameters. Alternatively, model fitting subsystem 132 is configured to train a neural network model that can predict optical absorption coefficients, optical scattering coefficients and the layer thicknesses in a multilayer tissue structure.

In some embodiments, model fitting subsystem 132 is further configured to use the trained machine-learning model to generate real-time estimated optical absorption and scattering coefficients 140 for each layer in maternal-fetal multilayer structure 136 at each wavelength $\lambda_1$ and $\lambda_2$, based on the time-resolved reflectance curve 138. After receiving estimated optical absorption and scattering coefficients 140, oxygen saturation extraction subsystem 134 is configured to estimate oxygen saturation levels 142 for the mother and fetus based on Eqns. (1) and (4) in this patent disclosure, by using the estimated optical absorption and scattering coefficients 140. In some embodiments, model fitting subsystem 132 and oxygen-saturation-extraction subsystem 134 can be implemented with computer program code. However, some or all functionalities of model fitting subsystem 132 and oxygen-saturation-extraction subsystem 134 can also be implemented with hardware modules such as application-specific integrated circuit (ASIC) chips, field-programmable gate arrays (FPGAs), and artificial intelligent (AI) chips.

Note that by using transabdominal fetal oximetry system 100 and, in particular, FMCW near-infrared spectroscopy 130, absolute concentrations of the oxygenated hemoglobin and deoxygenated hemoglobin for both mother and fetus can be extracted and the oxygen saturation levels for both the mother and fetus can be determined in real-time with high accuracy. Consequently, transabdominal fetal oximetry system 100 using FMCW near-infrared spectroscopy 130 and data processing subsystems 132 and 134 provide a significantly improved solution over the conventional two-wavelength CW transabdominal fetal pulse techniques described above.

FMCW Timing-Domain Spectroscopy

Figures 2A, 2B, 2C, 2D:
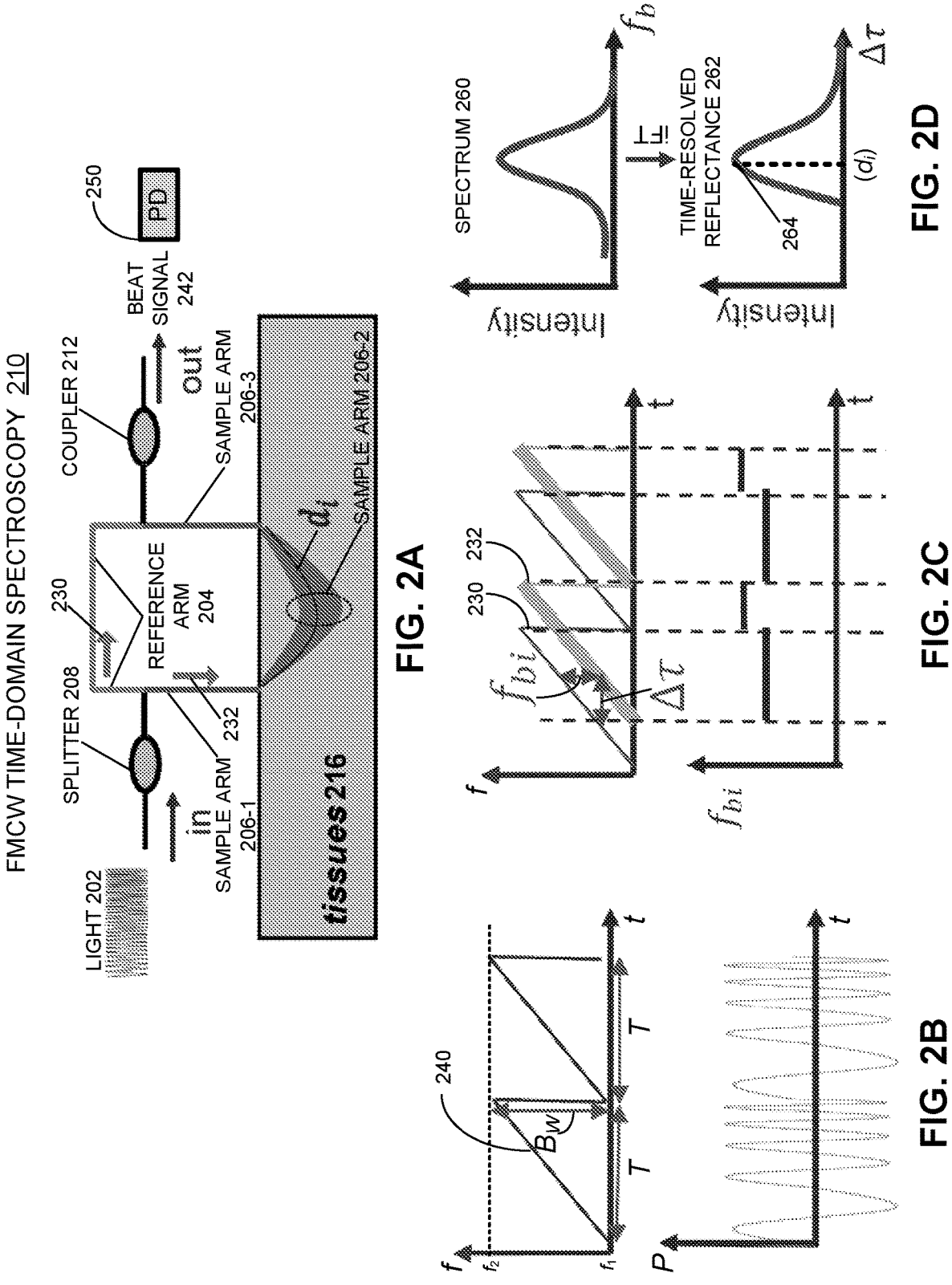
FIG. 2A shows a simplified FMCW time-domain spectroscopy for transabdominal fetal oximetry measurements with a single light source on a single layer of tissues, in accordance with the disclosed embodiments.
FIG. 2B shows an exemplary (top plot) frequency modulation waveform used to sweep the frequency of the probe light in the exemplary FMCW time-domain spectroscopy in accordance with the disclosed embodiments; and (bottom plot) the phase of the light source in the exemplary FMCW time-domain spectroscopy, in accordance with the disclosed embodiments.
FIG. 2C illustrates (top plot) the relative frequency of the reference light and the sample light in the exemplary FMCW spectroscopy at the coupler, in accordance with the disclosed embodiments; and (bottom plot) the beating frequency of the reference light and the sample light in the exemplary FMCW spectroscopy at the photodetector in accordance with the disclosed embodiments
FIG. 2D illustrates (top plot) an exemplary spectrum of the generated beat frequencies $f_b$ for the band of light paths within the sample arm in accordance with the disclosed embodiments; and (bottom plot) an exemplary time-resolved reflectance curve derived from the spectrum of the beat frequencies $f_b$, in accordance with the disclosed embodiments.

We now discuss the operating principles of the disclosed FMCW time-domain spectroscopy in the disclosed transabdominal fetal oximetry system. Specifically, FIG. 2A shows a simplified FMCW time-domain spectroscopy 210 (or "FMCW spectroscopy 210") for transabdominal fetal oximetry measurements with a single light source 202 on a single layer of tissues 216 in accordance with the disclosed embodiments. As can be seen in FIG. 2A, at the input side of FMCW spectroscopy 210, a probe light 202, which is typically generated by a laser, is split by splitter 208 into a reference light 230 propagating in a reference arm 204 and a sample light 232 guided by sample arm 206 toward a layer of tissues 216. In some embodiments, reference arm 204 is composed of one or more sections of optic fiber having a known combined length $L_0$. Hence, reference light 230 propagates a path length 4 from splitter 208 and arrives at coupler 212 at the output side of FMCW spectroscopy 210.

In some embodiments, sample arm 206 is composed of an input section 206-1 and an output section 206-3 having a combined path length $L_0$. However, sample arm 206 includes an additional section inside the layer of tissues 216, wherein sample light 232 takes a multitude of paths to travel from the end of input section 206-1 to the beginning of output section 206-3. The multitude of light paths taken by sample light 232 inside tissues 216 are collectively referred to as "sample arm 206-2." After propagating through the three sections 206-1, 206-2, and 206-3 of the sample arm 206 and arriving at coupler 212, sample light 232 in sample arm 206 travels a longer distance than the total path length traveled by reference light 230 in reference arm 204, wherein the additional distance depends on the particular optical path in sample arm 206-2. For example, for the highlighted $i^{th}$ optical path in sample arm 206-2, sample light 232 travels an additional path length of $d_i$ compared to the reference arm distance $L_o$ traveled by reference light 230.

Moreover, in FMCW spectroscopy 210, the wavelength/frequency of probe light 202 is continuously modulated in time, such that the wavelength/frequency of probe light 202 sweeps periodically between a predetermined low value and a predetermined high value. FIG. 2B shows an exemplary frequency modulation waveform 240 used to sweep the frequency of probe light 202 in FMCW time-domain spectroscopy 210 in accordance with the disclosed embodiments. As can be seen in FIG. 2B, the frequency (f) of probe light 202 is swept linearly with time t from the lowest frequency $f_1$ to the highest frequency $f_2$ over a time period T, and repeated for every cycle of the time period T. Hence, T is referred to as the "sweeping period," wherein the frequency sweeping bandwidth/range $f_2-f_1$ is denoted as "$B_w$."

Note that even though in FIG. 2B the frequency of the probe light 202 is modulated linearly with time, other embodiments of the frequency modulation schemes for probe light 202 in the disclosed FMCW spectroscopy can be based on other modulation waveforms (e.g., other linear waveforms or non-linear waveforms) without departing from the scope of the present technique. Note that FIG. 2B also shows the laser phase P vs. time t plot (bottom plot in FIG. 2B) corresponding to the above-described frequency modulation scheme (top plot). As can be seen in the phase vs. time plot, the laser phase is also modulated periodically as a result of the periodic frequency sweeping.

FIG. 2C illustrates the frequency of reference light 230 and sample light 232 in FMCW spectroscopy 210 at coupler 212 in accordance with the disclosed embodiments. Using the $i^{th}$ light path having the path length of $d_i$ as an example, it can be seen in the top plot of FIG. 2C that, because of the extra path length $d_i$ traveled by sample light 232, sample light 232 and reference light 230 are separated by a time delay $\Delta\tau$ caused by the extra path length d; in the sample arm 206. At coupler 212, the two frequency-swept signals 230 and 232 are mixed which leads to an interference between light 230 and 232. The interference of the two signals produces beat signal 242 as the output of FMCW spectroscopy 210. Note that the frequency $f_{bi}$ of beat signal 242 is proportional to the time delay $\Delta\tau$, which is itself proportional to the additional path length d; in the tissues 216. This beat frequency $f_{bi}$ can be expressed as:

$$f_{bi} = S \times \frac{d_i}{v}, \tag{2}$$

wherein v is the speed of light in tissues 216, and S is the slope of frequency-sweeping waveform 240, which is given by:

$$S = \frac{B_W}{T}. \tag{3}$$

The beat frequency $f_{bi}$ vs. time t plot for the $i^{th}$ optical path is shown in the bottom plot of FIG. 2C.

Note that a photodetector (PD) 250 positioned at the output of FMCW spectroscopy 210 can be used to detect an average intensity of beat signal 242. Recall that sample arm 206-2 in FMCW spectroscopy 210 is composed of a band of light paths of different path-lengths as a result of scattering and reflection in tissues 216. Hence, based on Eqns. (2) and (3), the outputs of PD 250 can be used to generate a plot of detected signal intensities of the band of light paths 206-2 vs. the corresponding beat frequencies $f_b$. This plot represents the spectrum for the band of beat frequencies $f_b$. Because different light paths result in different beat frequencies $f_b$, this spectrum plot can be used to resolve the group of light paths in sample arm 206-2.

FIG. 2D illustrates an exemplary spectrum 260 (top plot) of the generated beat frequencies $f_b$ for the band of light paths within sample arm 260-2 in accordance with the disclosed embodiments. Note that exemplary spectrum 260 shows that the contributions from different path lengths in sample arm 206-2 have a bell-shaped distribution. By performing an inverse Fourier Transform (iFT) on spectrum 260, a TOF/time-resolved reflectance curve (i.e., the reflected intensity vs. time delay $\Delta\tau$ relationship for the band of light paths in sample arm 206-2) can be obtained.

FIG. 2D further illustrates an exemplary time-resolved reflectance curve 262 (bottom plot) derived from spectrum 260 for the band of light paths in sample arm 206-2 in accordance with the disclosed embodiments. From this reflectance curve 262, it can be observed that the band of light paths in sample arm 206-2 has a time-resolved distribution. In other words, each intensity value in time-resolved reflectance curve 262 can be mapped to a particular light path in sample arm 206-2. For example, reflectance curve 262 shows a near peak value 264 which corresponds to the $i^{th}$ light path $d_i$.

Note that using FMCW spectroscopy 210 to resolve the band of light paths in sample arm 206-2 in the time domain based on their associated time delays is a significant improvement over the conventional CW transabdominal fetal pulse techniques which can only measure an average intensity of the group of light paths in sample arm 206-2. In addition, the time delays $\Delta\tau$ from the time-resolved reflectance curve can also be used to determine the associated optical path lengths, e.g., by multiplying a given A-rand the speed of light v in tissues 216. In some embodiments, the disclosed FMCW time-domain spectroscopy can be combined with the conventional CW transabdominal fetal pulse oximetry to improve the oxygen saturation estimation accuracies of the conventional CW transabdominal fetal pulse oximetry (described in more detail below).

Generally speaking, a larger frequency sweeping bandwidth/range ($B_w$) of probe light 202 effectuates a higher temporal resolution in time-resolved reflectance curve 262. In other words, using a larger sweeping range B, different light paths in sample arm 206-2 can be more precisely differentiated or resolved in reflectance curve 262. Consequently, more light paths in sample arm 206-2 can be resolved in reflectance curve 262. In contrast, when a smaller sweeping range B is used, more light paths in sample arm 206-2 are averaged into a single data point within reflectance curve 262. In practice, the maximum sweeping range B is limited by the sweeping range of the laser source that generates probe light 202. In some embodiments, a frequency sweeping range $B_w$ within a frequency range of $[3\times10^{10}$ Hz-$7\times10^{11}$ Hz] has been found to be sufficiently good. For example, one measurement setup used a frequency sweeping range $B_w=5.6\times10^{10}$ Hz to generate good measurement results.

The disclosed FMCW time-domain spectroscopy and the disclosed TFO based on the disclosed FMCW spectroscopy can determine time-resolved reflectance values and optical path-lengths for a band of light paths because of two principal design features described above in conjunction with FIGS. 2A-2D: (1) the FMCW time-domain spectroscopy includes at least one frequency-swept light source; and (2) the FMCW time-domain spectroscopy is configured as an optical interferometer for the at least one frequency-swept light source. More specifically, to set up the interferometer operation for the at least one frequency-swept light source, the frequency-swept light source is divided into a reference signal and a sample signal prior to performing a TFO measurement. The sample signal is then used to probe a multilayer tissue structure which results in a band of time-delayed reflected signals which is coupled back into the FMCW time-domain spectroscopy. Finally, the original reference signal and the band of time-delayed reflected signals, which all have the same center wavelength, are mixed to effectuate interference. The resulting beat signals from the interference process are used to construct the time-resolved reflectance curve for the band of time-delayed reflected signals.

To enable accurate TFO measurements in a maternal-fetal multilayer tissue structure, instead of using a single frequency-swept light source at a single central wavelength, embodiments of the disclosed FMCW time-domain spectroscopy employ two frequency-swept light sources of two different central wavelengths $\lambda_1$ and $\lambda_2$ as two probe lights to perform the above described time-resolved reflectance curve measurements. As mentioned above and described in more detail below, using two frequency-swept light sources of two different central wavelengths in the FMCW time-domain spectroscopy to perform TFO measurements allows absolute concentrations of the oxygenated hemoglobin and deoxygenated hemoglobin for both mother and fetus to be extracted, and the oxygen saturation levels for both the mother and fetus can be determined in real-time with high accuracy.

FMCW Spectroscopy-Based TFO Systems

Figure 3:
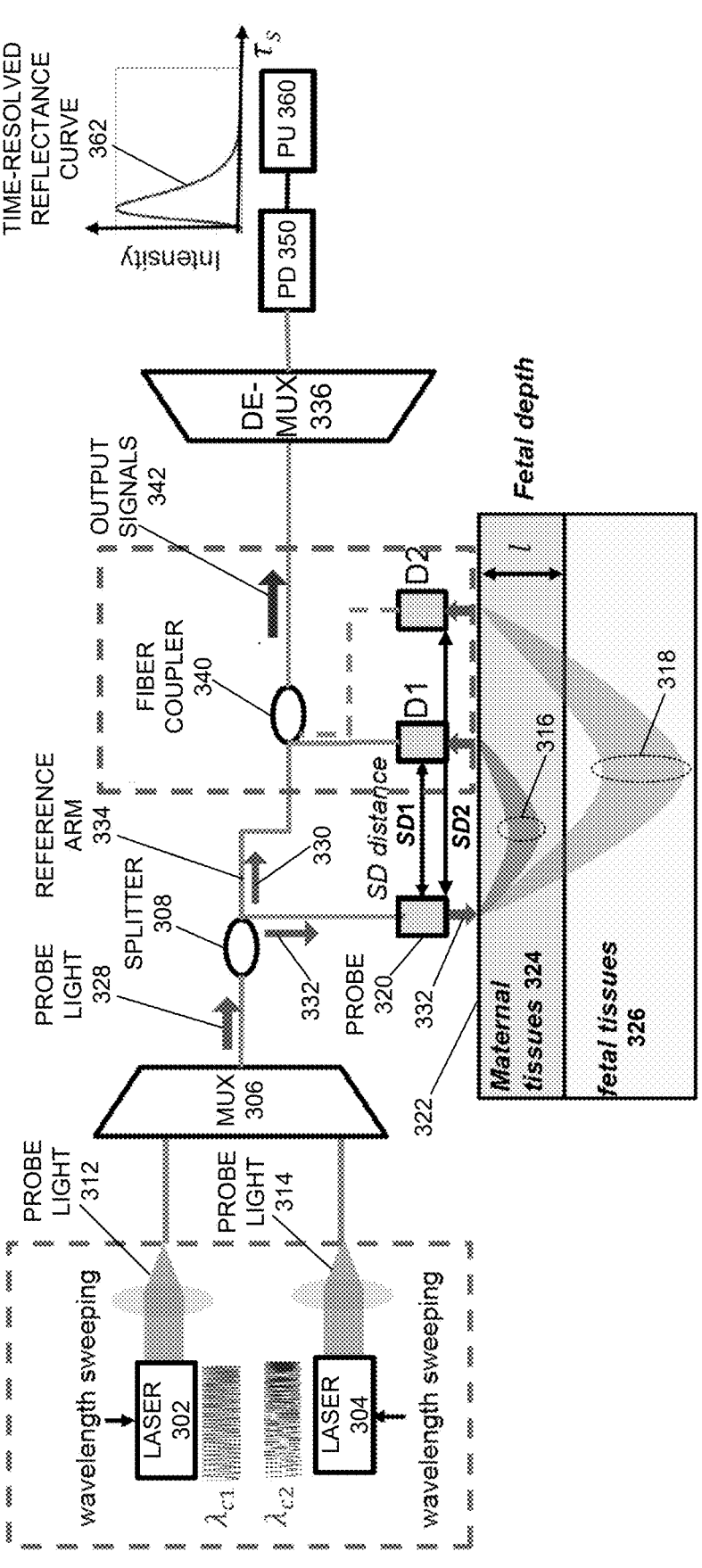
FIG. 3 illustrates a FMCW-based transabdominal fetal oximetry (TFO) system that implements source frequency sweeping and interferometer operations to generate time-resolved reflectance curves, in accordance with the disclosed embodiments in accordance with the disclosed embodiments.

FIG. 3 illustrates a FMCW time-domain spectroscopy-based TFO system 300 (or simply "FMCW-based TFO system 300" hereinafter) that implements source frequency sweeping and interferometer operations to generate time-resolved reflectance curves in accordance with the disclosed embodiments. As can be seen in FIG. 3, FMCW-based TFO system 300 includes two lasers 302 and 304 (also referred to as "light sources 302 and 304" hereinafter), which emit laser lights at center wavelengths $\lambda_1$ and $\lambda_2$, respectively. In various embodiments, both wavelengths $\lambda_1$ and $\lambda_2$ are in the infrared region, and more specifically in the near infrared region. In such embodiments, FMCW-based TFO system 300 is a near-infrared spectroscopy. For example, $\lambda_1$ and $\lambda_2$ can be 800 nm and 830 nm, respectively. Similar to FMCW time-domain spectroscopy 210, the laser lights emitted by light sources 302 and 304 are wavelength/frequency modulated around the respective center wavelengths $\lambda_1$ and $\lambda_2$ by using the wavelength/frequency sweeping techniques described above in conjunction with FIGS. 2A-2D, thereby generating modulated probe lights 312 and 314, respectively. Note that in addition to using the sawtooth frequency sweeping technique shown in FIG. 2B, other linear waveforms, such as a triangular waveform, can be used to sweep the wavelengths/frequencies of the emitted laser lights from light sources 302 and 304. In some embodiments, the wavelengths/frequencies of light sources 302 and 304 can be swept with non-linear waveforms, such as sinusoidal or square waveforms without departing from the general scope of the present technique. In various embodiments, wavelengths/frequencies of light sources 302 and 304 can be tuned using one of the following tuning mechanisms: current tuning, temperature tuning, microelectromechanical systems (MEMS)-based tuning, and fiber-grating-based tuning, among other tuning mechanisms.

Next, the modulated probe lights 312 and 314 are combined/multiplexed at a multiplexer (MUX) 306 based on a particular multiplexing scheme to generate a multiplexed probe light 328. For example, MUX 306 can be configured to perform one of the following multiplexing schemes: a wavelength-division multiplexing scheme, a time-division multiplexing scheme, and a frequency-division multiplexing scheme. The multiplexed probe light 328 is then split by a splitter 308 into (1) a reference light 330 that propagates through a reference arm 334 having a predetermined optical-path length, and (2) a sample light 332 that is guided toward the maternal-fetus tissue structure. As described above, splitting probe light 328 into reference light 330 and sample light 332 sets up the subsequent interference operation. In various embodiments, splitter 308 can be implemented with a first fiber coupler.

As shown in FIG. 3, FMCW-based TFO system 300 includes a probe 320 positioned on a maternal abdomen surface 322 to direct incident sample light 332 through a first combined layer of maternal tissues 324 (which can include multiple layers of maternal tissues) toward a second combined layer of fetal tissues 326 (which can include multiple layers of fetal tissues) of a fetus. In some embodiments, probe 320 can be implemented with a second fiber coupler configured to focus the sample light 332 on maternal abdomen surface 322. Note that incident sample light 332 passes through the entire depth of maternal tissues 324, including vascular tissues of the mother, and at least a portion of fetal tissues 326, including vascular tissues of the fetus. Sample light 332 is scattered in both the maternal tissues 324 and the fetal tissues 326, including being scattered by the vascular tissues of the mother and the fetus.

In maternal tissues 324, the scattered light of incident sample light 332 forms light band 316 of different path lengths. Light band 316 can be denoted as $\langle L_{mat} \rangle_{\lambda 1}$ and $\langle L_{mat} \rangle_{\lambda 2}$ to represent separate contributions from two different wavelengths $\lambda_1$ and $\lambda_2$ and to distinguish from the light paths in fetal tissues 326. Note that a first detector D1 is positioned on the maternal abdomen surface 322 to receive the light band 316 that traverses maternal tissues 324 and reemerges on the maternal abdomen surface 322. In some embodiments, first detector D1 can be implemented with a third fiber coupler (which collects the light band 316 entering the free-space into a fiber). Note that probe 320 and the first detector D1 are separated from each other by the first source-detector distance SD1. In some embodiments, first detector D1 is positioned on maternal abdomen surface 322 at an optimal location where the highest signal strength corresponding to the reemerged light band 316 can be obtained. Note that once the position of D1 is fixed, SD1 becomes a known value that will be used as an input parameter for post-measurement TFO data processing. Note that optical signals generated based on the received light band 316 comprise contributions primarily from maternal tissues 324.

Separately in fetal tissues 326, a portion of incident sample light 332 that traverses the entire depth of maternal tissues 324 and also a portion of or the entire depth of fetal tissues 326, is scattered in fetal tissues 326, and the scattered light forms light band 318 of different path lengths. Light band 318 can be denoted as $\langle L_{fet} \rangle_{\lambda 1}$ and $\langle L_{fet} \rangle_{\lambda 2}$ to represent separate contributions from two wavelengths $\lambda_1$ and $\lambda_2$ and to distinguish from the light signals produced in maternal tissues 324. Note that a second detector D2 is positioned on the maternal abdomen surface 322 further away from probe 320 to receive the light band 318 that traverses both maternal tissues 324 and fetal tissues 326 and reemerges on maternal abdomen surface 322. In some embodiments, second detector D2 can be implemented with a fourth fiber coupler (which collects the light band 318 in the free-space into another fiber). Note that probe 320 and the second detector D2 are separated from each other by the second source-detector distance SD2 greater than the first source-detector distance SD1. In some embodiments, second detector D2 is positioned on maternal abdomen surface 322 at an optimal location where the highest signal strength corresponding to the reemerged light band 318 can be obtained. Note that once the position of D2 is fixed, SD2 becomes a known value that will be used as another input parameter for post-measurement TFO data processing. Note also that optical signals generated based on the received light band 318 comprise contributions from both maternal tissues 324 and fetal tissues 326.

The optical signals 316 and 318 collected by first detector D1 and second detector D2 are then mixed at fiber coupler 340 with the reference light 330 that has traversed reference arm 334. As described above, the received light band 316 that includes a sub-band $\langle L_{mat} \rangle_{\lambda 1}$ and a sub-band $\langle L_{mat} \rangle_{\lambda 2}$ carrying maternal signals will interfere independently with the two wavelength components within reference light 330. Separately, the received light band 318 that includes a sub-band $\langle L_{fet} \rangle_{\lambda 1}$ and a sub-band $\langle L_{fet} \rangle_{\lambda 2}$ caring mixed maternal-fetal signals will also interfere independently with the two wavelength components within reference light 330. Note that these two mixing-interference processes can be separated in the time-domain because received light band 316 and received light band 318 can arrive at fiber coupler 340 at different times due to the difference in the path delays associated with received light band 316 and received light band 318. As a result of the interference process, outputs from fiber coupler 340 will include output signals 342 comprising various beat frequencies given by Eqns. (2) and (3) described above. Moreover, these signals include contributions from both modulated probe lights 312 and 314 at respective center wavelengths $\lambda_1$ and $\lambda_2$. In some embodiments, a demultiplexer (DEMUX) 336 can be placed in FMCW-based TFO system 300 after fiber coupler 340 to separate/demultiplex output signals into a first group associated with the first wavelength $\lambda_1$ and a second group associated with the second wavelength $\lambda_2$. However, as will be described in more detailed below, depending on the particular multiplexing scheme used by MUX 306, DEMUX 336 does not have to be used. For example, DEMUX 336 is not required when a time-division multiplexing scheme is used at MUX 306 (see FIG. 5).

Further down the path of FMCW-based TFO system 300 is PD 350, which receives optical signals 342 and converts optical signals 342 into electrical signals. The electrical signals from PD 350 are received by a processing unit 360 that includes one or more processors. As described above in conjunction with FIGS. 2A-2D, processing unit 360 is configured to perform frequency-domain filtering operations to generate a frequency spectrum including various beat frequencies corresponding to various different path lengths within received light band 316 and received light band 318. Processing unit 360 is further configured to generate a time-resolved reflectance curve 362 based on the generated frequency spectrum for both central wavelength $\lambda_1$ and $\lambda_2$. In other words, the generated time-resolved reflectance curve 362 is in fact composed of two time-resolved reflectance curves: one curve for each of the two probe lights with central wavelength $\lambda_1$ or $\lambda_2$. Note also that each of these two time-resolved reflectance curves for central wavelength $\lambda_1$ or $\lambda_2$ within generated time-resolved reflectance curve 362 contains the information for both light band 316 and light band 318. Using the above-described configuration of FMCW-based TFO system 300, this time-resolved reflectance curve 362 not only resolves in time for the different path lengths within each band of received light bands 316 and 318 and for each of the two probe lights with central wavelength $\lambda_1$ or $\lambda_2$, but also generates two well-separated time-resolved reflectance curves for the received light bands 316 and 318 that do not overlap with each other for each central wavelength $\lambda_1$ or $\lambda_2$.

As described above, time-resolved reflectance curve 362 is a function of the optical absorption coefficient and the optical scattering coefficient, as well as the thickness of each of layers 324 and 326. To extract these coefficients from time-resolved reflectance curve 362, a simulated reflectance curve is also derived by using a multilayer tissue model based on diffusion equations. The experimental measured time-resolved reflectance curve 362 is then fitted to the numerically simulated time-resolved reflectance curve through a nonlinear fitting technique. As a result, the absolute values of optical scattering and absorption coefficients associated with (1) each of maternal tissues 324 and fetal tissues 326 and (2) each of two wavelengths $\lambda_1$ and $\lambda_2$ can be obtained.

Specifically, for fetal tissues 326, the following five values can be extracted after model fitting:

$\mu_{\alpha2,\lambda1}$ which is the optical absorption coefficient of fetal tissues 326 corresponding to wavelength $\lambda_1$;

$\mu'_{s2,\lambda1}$ which is the optical reduced scattering coefficient of fetal tissues 326 corresponding to wavelength $\lambda_1$.

$\mu_{\alpha2,\lambda2}$ which is the optical absorption coefficient of fetal tissues 326 corresponding to wavelength $\lambda_2$;

$\mu'_{s2,\lambda2}$ which is the optical reduced scattering coefficient of fetal tissues 326 corresponding to wavelength 4; and $l_2$ which is the thickness of fetal tissues 326.

Similarly for maternal tissues 324, the following five values are extracted after model fitting:

$\mu_{\alpha1,\lambda1}$ which is the optical absorption coefficient of maternal tissues 324 corresponding to wavelength $\lambda_1$;

$u'_{s1,\lambda1}$ which is the optical reduced scattering coefficient of maternal tissues 324 corresponding to wavelength $\lambda_1$;

$\mu_{\alpha1,\lambda2}$ which is the optical absorption coefficient of maternal tissues 324 corresponding to wavelength $\lambda_2$;

$\mu'_{s1,\lambda2}$ which is the optical reduced scattering coefficient of maternal tissues 324 corresponding to wavelength $\lambda_2$; and $l_1$ which is the thickness of maternal tissues 324.

Next, the oxygenated ([☐☐☐ 2])) and deoxygenated ([ ☐☐ ]) hemoglobin concentration for the mother and/or the fetus can be derived based on the following equations:

$$\mu_{a,\lambda_1} = \epsilon_{\lambda_1}^{HbO_2}[HbO_2] + \epsilon_{\lambda_1}^{Hb}[Hb] \qquad (4)$$

$$\mu_{a,\lambda_2} = \epsilon_{\lambda_2}^{HbO_2}[HbO_2] + \epsilon_{\lambda_2}^{Hb}[Hb]$$

wherein $$\varepsilon_{\lambda}^{HbO_2}$$

and $$\varepsilon_{\lambda}^{Hb}$$

are the extinction coefficients at a given wavelength of $\lambda_1$ or $\lambda_2$ for [☐☐☐ 2] and [☐☐ ], respectively, and can be looked up from the literature. Finally, the oxygen saturation levels ($SO_2$) for both the mother and the fetus can be computed as the ratio of oxygenated hemoglobin concentration ([☐☐☐ 2]) and total hemoglobin concentration ([☐☐☐ ]=[☐☐☐ 2]+[ ☐☐ ]: $SO_2$=[☐☐☐ $_2$]/[☐☐☐ ]. Note that in the above computation for the oxygen saturation levels, the optical reduced scattering coefficients $\mu'_{s,\lambda}$ are not used because they are significantly less important than the optical absorption coefficients $\mu_{\alpha,\lambda}$.

We now describe a number of detailed implementations of FMCW-based TFO system 300 based on different multiplexing schemes.

Figure 4:
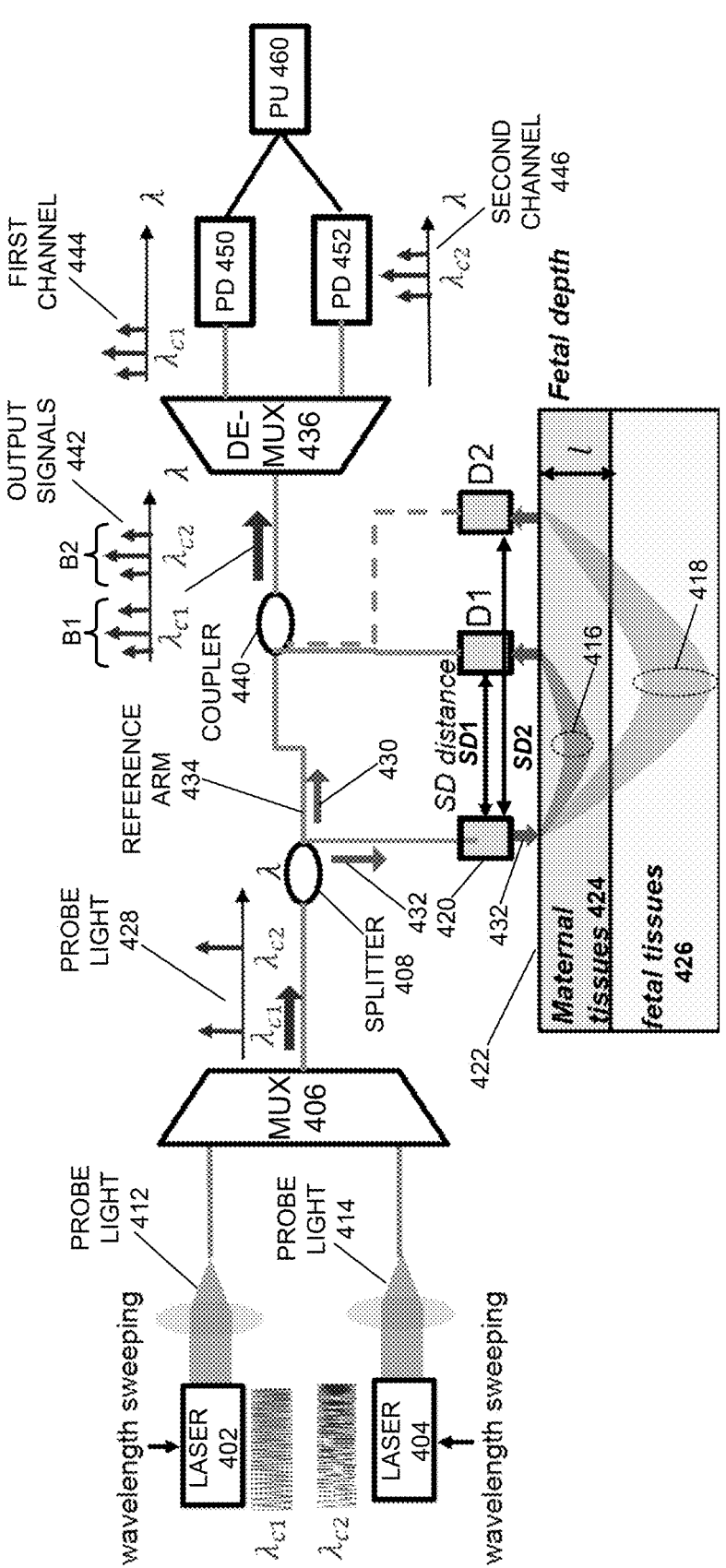
FIG. 4 illustrates an exemplary FMCW-based TFO system based on a wavelength division multiplexing scheme, in accordance with the disclosed embodiments.

FIG. 4 illustrates an exemplary FMCW time-domain spectroscopy-based TFO system 400 (or simply "FMCW-based TFO system 400" hereinafter) based on a wavelength division multiplexing scheme in accordance with the disclosed embodiments. Note that FMCW-based TFO system 400 has substantially the same setup as FMCW-based TFO system 300 prior to a DEMUX 336. Hence, the discussion below will assume those like-numbered components in FMCW-based TFO system 400 (except for MUX 406 and DEMUX 436) have the same described functionalities as the corresponding components in FMCW-based TFO system 300. As such, the discussion below will focus on MUX 406 and DEMUX 436 and signal detection and data processing after DEMUX 436.

Identical to FMCW-based TFO system 300, FMCW-based TFO system 400 includes two lasers 402 and 404 (also referred to as "light sources 402 and 404" hereinafter), which emit laser lights at central wavelengths $\lambda_1$ and $\lambda_2$, respectively. Similarly, light sources 402 and 404 are wavelength/frequency modulated around the respective central wavelengths $\lambda_1$ and $\lambda_2$ by using the wavelength/frequency sweeping techniques described above in conjunction with FIGS. 2A-2D, thereby generating modulated probe lights 412 and 414, respectively.

In the particular embodiment of FMCW-based TFO system 400 shown in FIG. 4, modulated probe lights 412 and 414 have the same frequency sweeping bandwidth $B_w$ and the same frequency sweeping period T. However, in some other embodiments of FMCW-based TFO system 400, modulated probe lights 412 and 414 can have different frequency sweeping bandwidths $B_{w1}$ and $B_{W2}$. In some further embodiments of FMCW-based TFO system 400, modulated probe lights 412 and 414 can also have different frequency sweeping periods $T_1$ and $T_2$. In other words, modulated probe lights 412 and 414 can be modulated with different frequency sweeping rates $1/T_1$ and $1/T_2$ without departing from the present scope.

In the embodiment of FMCW-based TFO system 400, the two modulated probe lights 412 and 414 are simultaneously transmitted and combined/multiplexed at MUX 406 to generate a multiplexed probe light 428. Note that in multiplexed probe light 428, modulated probe lights 412 and 414 do not interfere with each other because they are sufficiently separated from each other by the different center wavelengths $\lambda_1$ and $\lambda_2$.

Multiplexed probe light 428 is then split by splitter 408 into (1) reference light 430, which propagates through a reference arm 434 of a predetermined optical-path length, and (2) sample light 432, which is guided toward and shone on the maternal abdomen surface 422 through probe 420. Sample light 432, including both modulated probe lights 412 and 414, is then used to probe the multiplayer structure comprising the first combined layer of maternal tissues 424 (which can include multiple layers of maternal tissues) and the second layer combined of fetal tissues 426 (which can include multiple layers of fetal tissues). Subsequently, light band 416 carrying primarily maternal signals is formed in maternal tissues 424 and received by the first detector D1, which is placed at a known SD1 distance from probe 420; separately, light band 418 carrying mixed maternal-fetal signals is formed in both maternal tissues 424 and fetal tissues 426 and received by the second detector D2 placed at a known SD2 distance from probe 420, wherein SD2>SD1.

The optical signals 416 and 418 collected by detectors D1 and D2 are then mixed at fiber coupler 440 with the reference light 430 that has traversed reference arm 434. As a result of the interference processes, the output from fiber coupler 440 includes output signals 442 comprising various beat frequencies given by Eqns. (2) and (3) described above. Note that FIG. 4 shows an exemplary signal spectrum of output signals 442, which includes at least two signal bands: (1) first signal band B1 comprising beat signals as a result of interference between the combined signals of 416 and 418 and reference light 430; and (2) second signal band B2 comprising beat signals as a result of interference between the combined signals of 416 and 418 and reference light 430. Note that in signal band B1, the generated beat signals are centered around the first source signal at source wavelength $\lambda_1$, and in signal band B2, the generated beat signals are centered around the second source signal at the source wavelength $\lambda_2$. Because of the sufficient separation between $\lambda_1$ and $\lambda_2$, there is no overlap between the two signal bands B1 and B2. Hence, the simple wavelength division multiplexing techniques of FMCW-based TFO system 400 allows for simultaneously detecting interference signals associated with the two probe lights 412 and 414.

FMCW-based TFO system 400 further includes a DEMUX 436 following coupler 440 to separate/demultiplex output signals 442 into two separate channels of signals 444 and 446, wherein the first channel of signals 444 includes only the first band of wavelengths centered around wavelength $\lambda_1$, and the second channel of signals 446 includes only the second band of wavelengths centered around wavelength $\lambda_2$. In various embodiments, DEMUX 436, which is used to separate combined output signals 442 into two wavelengths channels 444 and 446, can be implemented with one of the following wavelength filtering and demultiplexing mechanisms/devices: (1) a thin film filter; (2) a Bragg grating; (3) an arrayed waveguide grating; and (4) an interleaver.

In FMCW-based TFO system 400, following the first signal channel of wavelengths 444 is a first PD 450 that converts the received optical signals 444 into a first electrical signal. Simultaneously and in parallel, a second PD 452 in FMCW-based TFO system 400 is used to receive the second channel of wavelengths 446 and convert the received optical signals into a second electrical signal. The electrical signals from PDs 450 and 452 are received by a processing unit 460 that is configured to perform the above-described functionalities of processing unit 360 in FMCW-based TFO system 300, including but not limited to: (1) generating the time-resolved reflectance curve based on the detected electrical signals; (2) generating a simulated time-resolved reflectance curve; (3) extracting optical scattering and absorption coefficients for each layer of the maternal tissues 424 and fetal tissues 426 corresponding to each of the two wavelengths $\lambda_1$ and $\lambda_2$; and (4) determining hemoglobin concentrations and oxygen saturation levels ($SO_2$) for both the mother and the fetus.

Figure 5:
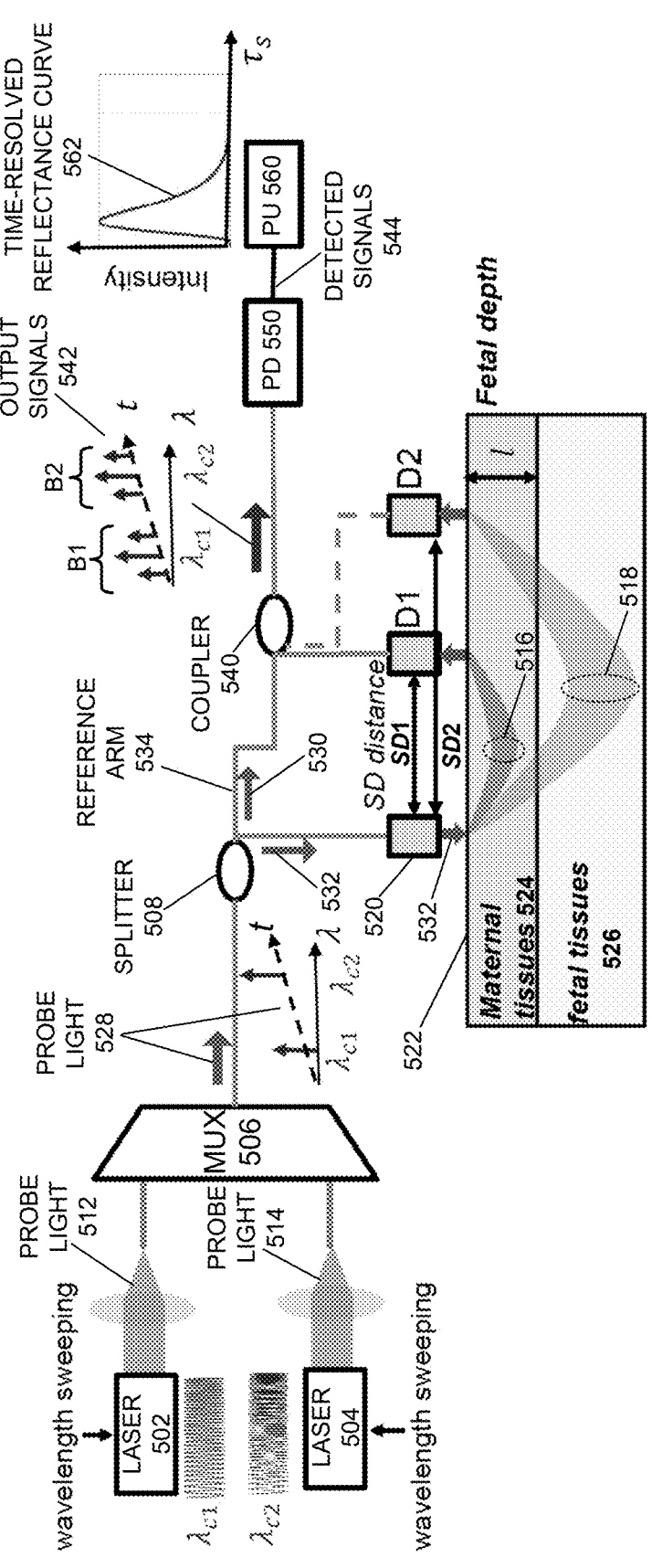
FIG. 5 illustrates an exemplary FMCW-based TFO system based on a time division multiplexing scheme, in accordance with the disclosed embodiments.

FIG. 5 illustrates an exemplary FMCW time-domain spectroscopy-based TFO system 500 (or simply "FMCW-based TFO system 500" hereinafter) based on a time division multiplexing scheme in accordance with the disclosed embodiments. Note that FMCW-based TFP system 500 has substantially the same setup as FMCW-based TFO system 400 but does not include a DEMUX. Hence, the discussion below will assume those like-numbered components in FMCW-based TFP system 500 (except for MUX 506) have the same described functionalities as the corresponding components in FMCW-based TFO system 400. As such, the discussion below will focus on MUX 506 and signal detection and data processing after coupler 540.

Identical to FMCW-based TFO system 300/400, FMCW-based TFO system 500 includes two lasers 502 and 504 (also referred to as "light sources 502 and 504" hereinafter), which emit laser lights at central wavelengths $\lambda_1$ and $\lambda_2$, respectively. Similarly, light sources 502 and 504 are wavelength/frequency modulated around the respective central wavelengths $\lambda_1$ and $\lambda_2$ by using the wavelength/frequency sweeping techniques described above in conjunction with FIGS. 2A-2D, thereby generating modulated probe lights 512 and 514, respectively.

In the particular embodiment of FMCW-based TFO system 500 shown in FIG. 5, modulated probe lights 512 and 514 have the same frequency sweeping bandwidth $B_w$, and the same frequency sweeping period T. However, in some other embodiments of FMCW-based TFO system 500, modulated probe lights 512 and 514 can have different frequency sweeping bandwidths $B_{w1}$ and $B_{w2}$. In some further embodiments of FMCW-based TFO system 500, modulated probe lights 512 and 514 can also have different frequency sweeping periods $T_1$ and $T_2$. In other words, modulated probe lights 512 and 514 can be modulated with different frequency sweeping rates $1/T_1$ and $1/T_2$ without departing from the present scope.

In the illustrated embodiment of FMCW-based TFO system 500, the two modulated probe lights 512 and 514 are simultaneously transmitted and combined/multiplexed at MUX 506 to generate a multiplexed probe light 528.

In FMCW-based TFO system 500, MUX 506 is configured to perform a time-division multiplexing (TDM) operation on modulated probe lights 512 and 514 by transmitting modulated probe lights 512 and 514 in different assigned time slots in the multiplexed probe light 528. For example, probe lights 512 and 514 can be alternatively selected and transmitted in alternating and equal duration time slots. In other words, probe light 512 is selected and transmitted during time slots TS1, TS3, TS5, TS7, etc., whereas probe light 514 is selected and transmitted during time slots TS2, TS4, TS6, TS8, etc. This produces multiplexed probe light 528 comprising a sequence of time slots with alternating wavelength: TS1($\lambda_1$), TS2($\lambda_2$), TS3($\lambda_1$), TS4($\lambda_2$), TS5($\lambda_1$), TS6($\lambda_2$), TS7($\lambda_1$), TS8 ($\lambda_2$), etc. FIG. 5 shows both exemplary signal-spectrum and time-domain plots of multiplexed probe light 528. As can be seen, the modulated probe lights 512 and 514 within multiplexed probe light 528 do not interfere with each other because they are separated in the time domain and by the different center wavelengths $\lambda_1$ and $\lambda_2$.

Multiplexed probe light 528 is then split by splitter 508 into (1) a reference light 530 that propagates through a reference arm 534 of a predetermined optical-path length; and (2) a sample light 532 that is guided toward and shone on the maternal abdomen surface 522 through probe 520. Sample light 532, including both modulated probe lights 512 and 514, is then used to probe the multiplayer tissue structure comprising the first combined layer of maternal tissues 524 (which can include multiple layers of maternal tissues) and the second combined layer of fetal tissues 526 (which can include multiple layers of fetal tissues). Subsequently, light band 516 carrying primarily maternal signals is formed in maternal tissues 524 and received by the first detector D1, which is placed at a known SD1 distance from probe 520; separately, light band 518 carrying mixed maternal-fetal signals is formed in both maternal tissues 524 and fetal tissues 526 and received by the second detector D2 placed at a known SD2 distance from probe 520, wherein SD2>SD1.

Optical signals 516 and 518 collected by detectors D1 and D2 are then mixed at fiber coupler 540 with the reference light 530 that traversed reference arm 534. As a result of the interference processes, the output from fiber coupler 540 includes output signals 542 comprising various beat frequencies given by Eqns. (2) and (3) described above. Note that FIG. 5 shows both exemplary signal-spectrum and time-domain plots of output signals 542. Similar to output signals 442, signal spectrum of output signals 542 includes at least two signal bands: (1) signal band B1 comprising beat signals as a result of interference between the combined signals of 516 and 518 and reference light 530; and (2) signal band B2 comprising beat signals as a result of interference between the combined signals of 516 and 518 and reference light 530. Again, in signal band B1, the generated beat signals are centered around the first source signal at source wavelength $\lambda_1$, and in signal band B2, the generated beat signals are centered around the second source signal at the source wavelength $\lambda_2$. There is no overlap between the two signal bands B1 and B2 in the signal spectrum.

Moreover, the exemplary time-domain plot of output signals 542 shows the same two signal bands fully separated in time as a result of using time-division multiplexing at MUX 506 to generate probe light 532. This means the tissue responses to the two modulated probe lights 512 and 514 are already time-resolved in output signals 542. As such, no additional demultiplexing/DEMUX of output signals 542 is needed. In other words, FMCW-based TFO system 500 based on the time-division multiplexing scheme does not need a separate DEMUX component. Instead, output signals 542 can be directly coupled to PD 550, which converts the received optical signals 542 into detected electrical signals 544. The detected signals 544 are received by processing unit 560, which is configured to perform the above-described functionalities of processing unit 360 in FMCW-based TFO system 300, including but not limited to: (1) generating the time-resolved reflectance curve 562 based on the detected signals 544; (2) generating a simulated time-resolved reflectance curve; (3) extracting optical scattering and absorption coefficients for each of the maternal tissues 524 and fetal tissues 526 corresponding to each of the two wavelengths $\lambda_1$ and $\lambda_2$; and (4) determining hemoglobin concentrations and oxygen saturation levels (SO$_2$) for the mother and the fetus.

Figure 6:
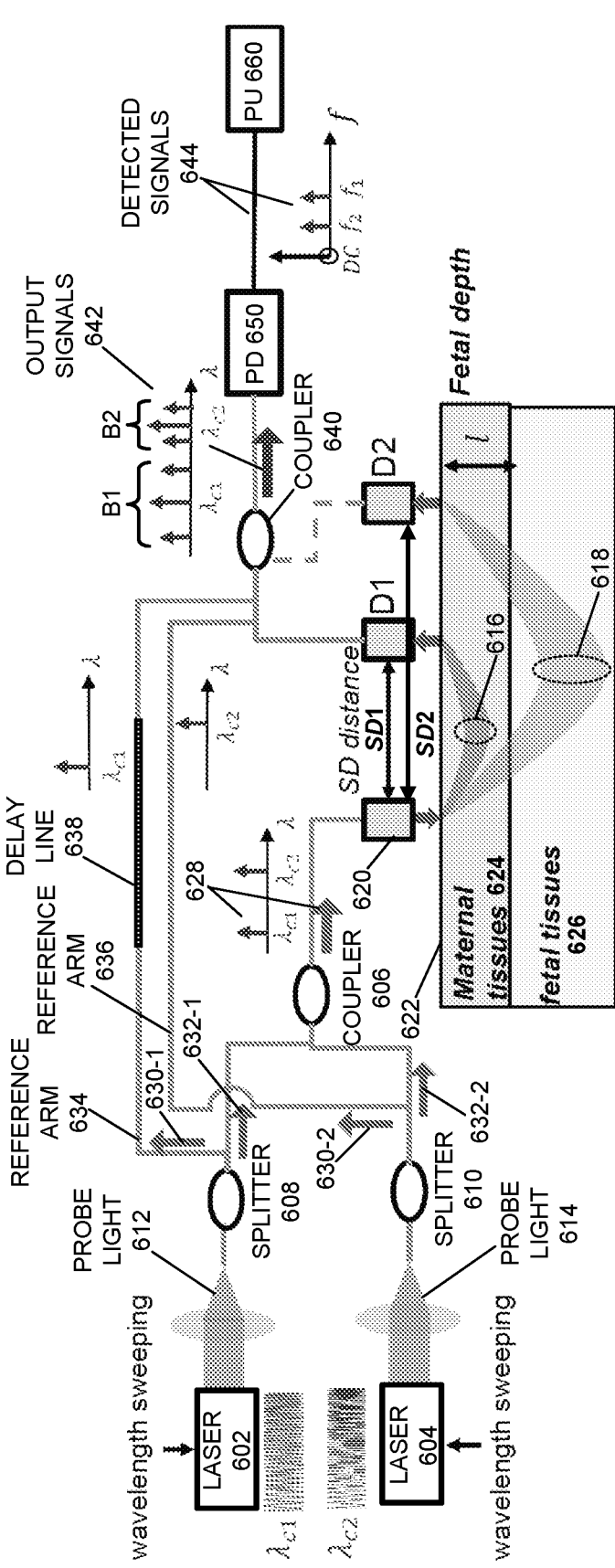
FIG. 6 illustrates an exemplary FMCW-based TFO system based on a frequency division multiplexing scheme, in accordance with the disclosed embodiments.

FIG. 6 illustrates an exemplary FMCW-based TFO system 600 based on a frequency division multiplexing scheme in accordance with the disclosed embodiments. Note that FMCW-based TFO system 600 is similar to FMCW spectroscopy 500 in that both do not require a DEMUX and only need one PD to convert optical signals to electrical signals. FMCW-based TFO system 600 also includes two lasers 602 and 604 (also referred to as "light sources 602 and 604" hereinafter), which emit laser lights at center wavelengths $\lambda_1$ and $\lambda_2$, respectively.

Similarly to FMCW-based TFO system 300/400/500, light sources 602 and 604 are wavelength/frequency modulated around the respective central wavelengths $\lambda_1$ and $\lambda_2$ by using the wavelength/frequency sweeping techniques described above in conjunction with FIGS. 2A-2D, thereby generating modulated probe lights 612 and 614, respectively. Moreover, light sources 602 and 604 are modulated with different frequency sweeping periods T$_i$ and T$_2$. In other words, modulated probe lights 612 and 614 have different frequency sweeping rates $1/T_1 \neq 1/T_2$. As an example, the frequency sweeping rates of modulated probe lights 612 and 614 can be set to $1/T_1=1$ kHz and $1/T_2=2.9$ kHz, respectively. This means one cycle of frequency sweep in modulated probe light 612 takes 1 ms, whereas one cycle of frequency sweep in modulated probe light 614 takes ~0.345 ms. Note that the above frequency sweeping rates are used for illustrative purposes but they should generally be set sufficiently far apart from each other.

In FMCW-based TFO system 600, each probe light of the two modulated probe lights 612 and 614 is split into a reference light and a sample light by a respective splitter 608 and 610. More specifically, splitter 608 divides probe light 612 into a first reference light 630-1 that propagates through a first reference arm 634, and a first sample light 632-1 that is guided toward a coupler 606. Separately and concurrently, splitter 610 divides probe light 614 into a second reference light 630-2 that propagates through a second reference arm 636, and a second sample light 632-2 that is guided toward coupler 606. Note that in FMCW-based TFO system 600, first reference arm 634 is configured to have a longer optical-path delay than reference arm 636 by including an extra section of delay line 638 (illustrated with a thicker and darker line segment) in first reference arm 634. We describe the effect and the advantage of adding delay line 638 in one of the reference arms in more detail below in conjunction with signal processing within FMCW-based TFO system 600.

At coupler 606, two sample lights 632-1 and 632-2 are combined/multiplexed by coupler 606 to generate wavelength-multiplexed sample light 628. Note that in multiplexed sample light 628, the two modulated sample lights 632-1 and 632-2 do not interfere with each other because they are sufficiently separated from each other by the different center wavelengths $\lambda_1$ and $\lambda_2$. Note also that coupler 606 in FMCW-based TFO system 600 performs the same wavelength-multiplexing operation as MUX 406 in FMCW-based TFO system 400.

Sample light 628 is guided toward and shone on the maternal abdomen surface 622 through probe 620. Sample light 628, including both modulated probe lights 612 and 614, is then used to probe the multilayer tissue structure comprising the first combined layer of maternal tissues 624 (which can include multiple layers of maternal tissues) and the second combined layer of fetal tissues 626 (which can include multiple layers of fetal tissues). Subsequently, light band 616 carrying primarily maternal signals is formed in maternal tissues 624 and received by first detector D1, which is placed at a known SD1 distance from probe 620; separately, ight band 618 carrying mixed maternal-fetal signals is formed in both maternal tissues 624 and fetal tissues 626 and received by second detector D2 placed at a known SD2 distance from probe 620, wherein SD2>SD1.

Next, at fiber coupler 640, the optical signals 616 and 618 collected by detectors D1 and D2 are combined with reference light 630-1 that has traversed reference arm 634, including an extra delay caused by delay line 638, and reference light 630-2 that has traversed reference arm 636 without additional delay. As a result of the interference processes, the output from fiber coupler 640 includes output signals 642 comprising various beat frequencies given by Eqns. (2) and (3) described above. Note that FIG. 6 shows an exemplary signal-spectrum of output signals 642, which is composed of two signal bands: (1) first signal band B1 comprising beat signals as a result of interference between the combined signals of 616 and 618 and reference light 630-1; and (2) second signal band B2 comprising beat signals as a result of interference between the combined signals of 616 and 618 and reference light 630-2. Similarly to FMCW-based TFO system 300 and FMCW spectroscopy 400, the generated beat signals in signal band B1are centered around $\lambda_1$, whereas the generated beat signals in signal band B2 are centered around $\lambda_2$.

However, it can be observed that the signal-spectrum of output signals 642 differs from those of output signals 442 in FIG. 4 and output signals 542 in FIG. 5. In both output signals 442 and output signals 542, the two signal bands B1 and B2 have substantially the same bandwidth, and the same beat frequency profile. This is based on the assumption that the two probe lights in systems 400 and 500 are modulated with the same frequency sweeping bandwidth and the same frequency sweeping period (although not required). Under such assumptions, and according to Eqns. (2) and (3), the maximum beat frequencies associated with both probe lights in systems 400 or 500 would be substantially the same, thereby resulting in the same bandwidth and frequency profile for the two signal bands B1 and B2.

Note that when the two signal bands B1 and B2 have the same bandwidth and frequency profile around the respective center wavelength $\lambda_1$ and $\lambda_2$, the detected signals associated with the two probe lights can substantially overlap each other in the frequency domain. However, this is not a problem for FMCW-based TFO system 400, because the two signal bands B1 and B2 are separated into two channels and independently detected and processed. It is also not a problem for FMCW spectroscopy 500, because the two signal bands B1 and B2 are separated in the time-domain and therefore can be easily distinguished in the time-domain.

In FMCW-based TFO system 600 however, the two signal bands B1 and B2 are not separated in the time-domain (no time-division multiplexing is used), nor separated into two wavelength channels (no wavelength-division multiplexing is used). However, recall that two probe lights 612 and 614 are modulated with different frequency sweeping periods/rates (e.g., 1-ms at 1-kHz vs. 0.345-ms at 2.9-kHz). According to Eqns. (2) and (3), the band of beat frequencies carrying the tissue response to probe light 612 will be fully separated from the band of beat frequencies carrying the tissue response to probe light 614. As a result, even though the two signal bands B1 and B2 are not separated in the time-domain and processed together using a single PD 650, the contributions from probe light 612/wavelength $\lambda_1$ in the generated electrical signal can be easily separated and distinguished from the contributions from probe light 614/wavelength $\lambda_2$ in the frequency domain. In other words, by using two significantly different frequency sweeping periods/rates in the modulated probe lights 612 and 614, FMCW-based TFO system 600 is effectively configured to operate in the frequency division multiplexing mode.

Hence, output signals 642 are directly fed into PD 650, which converts the received optical signals 642 into detected signals 644. By using the disclosed frequency division technique, detected signals 644 should include two separate frequency bands corresponding to light sources 602 and 604, respectively. This frequency division effect is illustrated in FIG. 6 as two separate central frequencies $f_1$ and $f_2$ in an exemplary frequency spectrum of detected signals 644. Based on the above-described process of generating frequency spectrum 260 in FIG. 2D for a single probe light, the frequency spectrum of detected signal 644 should include two bell-shaped distributions that are centered around frequencies $f_1$ and $f_2$, respectively. A person skilled in the art can appreciate that the separation/distance between the two bell-shaped distributions can be controlled by the difference between the two frequency sweeping rates at the two light sources.

Note that the frequency sweeping rate is related to the measurement/extraction speed. Generally speaking, one sweeping period T as shown in FIG. 2B is used to generate one time-resolved reflectance curve, and optical coefficient extractions from the reflectance curve should be completed within the given sweeping period. For example, for a 1 kHz sweeping rate, the system has 1 ms to generate the reflectance curve and complete the data extraction. If 10 kHz sweeping rate is used, a single measurement should be completed within 0.1 ms. In other words, there is one-to-one correspondence between each sweeping period and a unique reflectance curve and new oxygenation estimates.

Note that when using a faster frequency sweeping rate (e.g., 10 kHz), the disclosed FMCW-based TFO systems can complete each oxygenation measurement faster (e.g., every 0.1 ms), which means the system is capable of detecting biological changes with a finer time-resolution. In contrast, when using a lower frequency sweeping rate (e.g., 1 kHz), the measurements would have a lower time-resolution (e.g., 1 kHz rate means no biological changes within 1 ms can be identified). In practice, an ideal frequency sweeping rate can be determined based on the nature of the applications, and in particular based on whether there are slow changes in tissue properties or fast changes in tissue properties. Generally speaking, the frequency sweeping period should be selected such that it is significantly shorter than the time scales of the measured biological tissue changes (e.g., a fetal movement). For oxygenation measurements, because the maternal and fetal tissues do not involve fast changes (except for occasional fetal movement), a frequency sweeping rate (e.g., 10 kHz/0.1 ms) is considered reasonably fast. Note that if the frequency sweeping rate is set too fast, even though you can achieve a very high time-resolution, the system can become excessively expensive. In various embodiments, a practical range for the frequency sweeping rate is from 1 kHz to 10 kHz when factoring in different aspects of trade-offs.

In some embodiments, delay line 638 added to reference arm 634 can be used to further increase the beat frequencies associated with probe light 612 without affecting the beat frequencies associated with probe light 614. This effect is again explained by Eqn. (2). Hence, when delay line 638 is used, the separation/distance between the two bell-shaped distributions in the frequency spectrum of detected signals 644 for the two probe lights 612 and 614 can be further increased, thereby further enhancing the effect of frequency division/separation in FMCW-based TFO system 600. In some embodiments, when the frequency division technique of using different frequency sweeping rates at the sources can achieve a sufficient amount of signal/frequency separations in the detected signals 644, using a delay line such as delay line 638 within FMCW-based TFO system 600 can become optional. On the other hand, when the frequency division technique of using delay line 638 in reference arm 634 can achieve a sufficient amount of signal/frequency separations in the detected signals 644, using different frequency sweeping rates at the sources in FMCW-based TFO system 600 can be optional.

The detected signals 644 are subsequently received by processing unit 660, which is configured to perform the above-described functionalities of processing unit 360 in FMCW-based TFO system 300, including but not limited to: (1) generating the time-resolved reflectance curve based on the detected signals 644; (2) generating a simulated time-resolved reflectance curve; (3) extracting optical scattering and absorption coefficients for each of the maternal tissues 624 and fetal tissues 626 corresponding to each of the two wavelengths $\lambda_1$ and $\lambda_2$; and (4) determining hemoglobin concentrations and oxygen saturation levels ($SO_2$) for the mother and the fetus. Note that the time-resolved reflectance curve generated based on detected signals 644 (not shown), and more specifically based on the frequency spectrum of detected signals 644 after applying iFT, should also include two well-separated bell-shaped signal-intensity vs. time-delay $\Delta\tau$ distributions (i.e., two time-resolved reflectance curves) for the two probe lights 612 and 614, respectively.

We now describe detailed operations of processing units 460-660 that generate the oxygen saturation levels based on the time-resolved reflectance curves.

In various embodiments, after a time-resolved reflectance curve is generated (i.e., for each given frequency-sweeping period), the optical properties of the maternal and fetal tissues in the measured double-layer structure, mainly those optical absorption coefficients and optical reduced scattering coefficients, can be extracted. Note that for oxygen saturation measurements, the optical absorption coefficients are of much greater significance. A number of techniques can be used to extract these tissue absorption/reduced scattering coefficients. In some embodiments, an iterative optimization technique can be used. Generally speaking, the iterative optimization technique nonlinearly fits experimental measured time-resolved reflectance to that derived from Radiative Transfer Equation (RTE) in the diffuse approximation for a semi-infinite medium.

Figure 7:
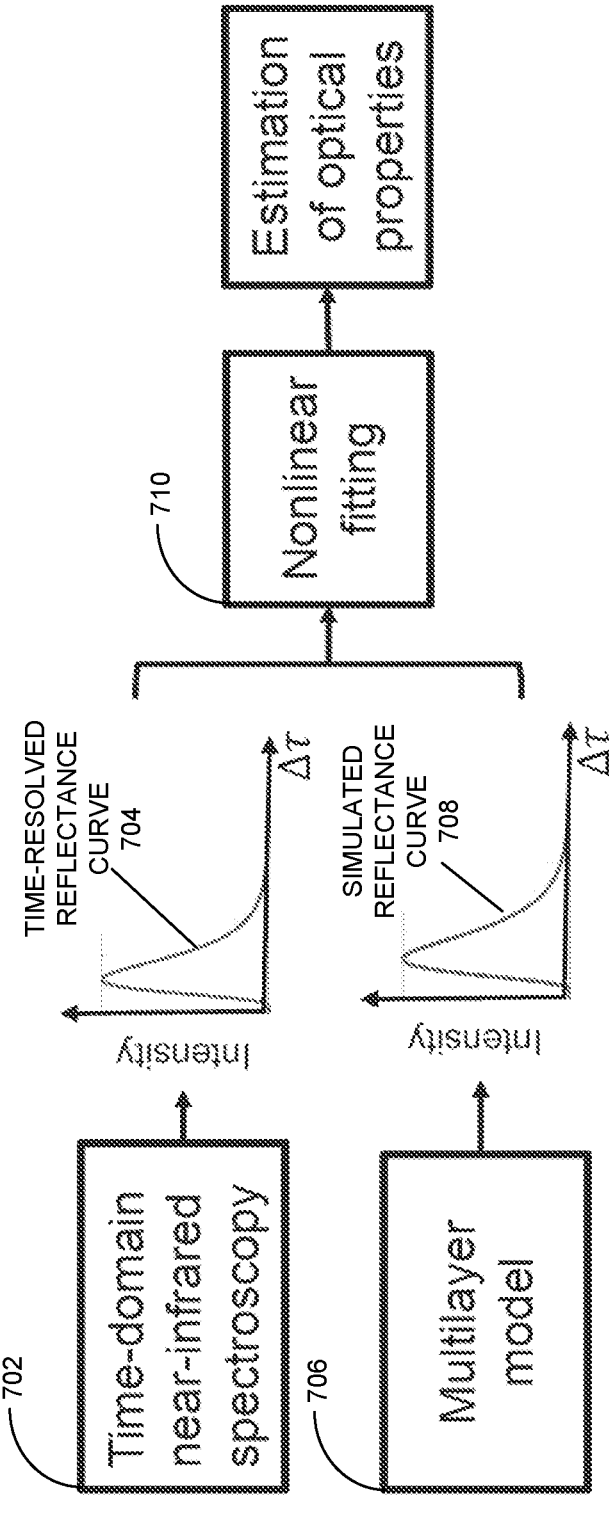
FIG. 7 shows a block diagram illustrating an iterative optimization process for extracting the optical properties from a multilayer tissue structure based on an experimental time-resolved reflectance curve generated by the disclosed FMCW time-domain spectroscopy, in accordance with the disclosed embodiments.

FIG. 7 shows a block diagram illustrating use of iterative optimization process 700 for extracting optical properties from a multilayer tissue structure based on an experimental time-resolved reflectance curve generated by the disclosed FMCW time-domain spectroscopy in accordance with the disclosed embodiments. In iterative optimization process 700, time-domain near-infrared spectroscopy 702 can be any of the above-described FMCW spectroscopy within systems 300, 400, 500, and 600. As in each of the above-described embodiments, time-domain spectroscopy 702 is used to generate experimental time-resolved reflectance curve 704. Parallel to generating reflectance curve 704, a simulated time-resolved reflectance curve 708 is derived from the diffusion approximation of reflectance in a multilayer semi-infinite tissue structure (also referred to as "multilayer tissue model 706" or "multilayer model 706"). Note that multilayer tissue model 706 is a function of optical absorption coefficients, optical scattering coefficients and the thickness of each layer in the simulated multilayer structure.

Next, the experimental measured reflectance curve 704 is fitted with the diffusion approximated reflectance curve 708 by a nonlinear fitting module 710, which includes an optimization algorithm configured to solve the optimization problem. In different embodiments, this optimization algorithm can be the Newton algorithm, Nelder-Mead simplex algorithm, Levenberg-Marquardt algorithm, gradient descent algorithm, and so on. Nonlinear fitting module 710 solves the optimization problem by minimizing the error function between the measured reflectance curve 704 and approximated reflectance curve 708. In various embodiments, the error function used can be mean square error, root mean square error, or some other error function technique. In some embodiments, nonlinear fitting module 710 employs an all-at-once approach by fitting all optical parameters $(\mu_{a,\lambda 1}, \mu'_{s1,\lambda 1}, \mu_{a1,\lambda 2}, \mu'_{s1,\lambda 2}, \mu_{a2,\lambda 1}, \mu'_{s2,\lambda 1}, \mu_{a2,\lambda 2}, \mu'_{s2,\lambda 2})$ to the multilayer model 706.

In other embodiments, nonlinear fitting module 710 can employ a stepwise fitting procedure to extract the optimal properties. For example, using a given stepwise fitting procedure, nonlinear fitting module 710 first fits part of the measured reflectance curve 704 collected by a detector having the shortest SD distance (e.g., SD1 in each of the disclosed embodiment) to the one-layered tissue model to obtain the optical properties $(\mu_{a,\lambda 1}, \mu'_{s1,\lambda 1}, \mu_{a1,\lambda 2}, \mu'_{s1,\lambda 2})$ of the first layer of tissues. Next, after $(\mu_{a,\lambda 1}, \mu'_{s1,\lambda 1}, \mu_{a1,\lambda 2}, \mu'_{s1,\lambda 2})$ are fixed, nonlinear fitting module 710 then fits another part of the measured reflectance curve 704 collected by a detector having the second shortest SD distance (e.g., SD2 in each of the disclosed embodiment) to the two-layered model to extract optical properties $(\mu_{a2,\lambda 1}, \mu'_{s2,\lambda 1}, \mu_{a2,\lambda 2}, \mu'_{s2,\lambda 2})$ of the second layer of tissues. This process continues if more layers exist and more than two detectors are used to collect the diffused-reflected light signals. By way of this stepwise fitting procedure, the optical properties of each layer can be sequentially deduced. Note that no matter which type of model fitting procedure is employed, iterative optimization process 700 based on nonlinear fitting generally becomes less accurate and more time consuming as the unknown parameters increase.

Besides the iterative optimization technique, a data-driven machine learning technique can be used to extract these tissue absorption/scattering coefficients. Generally speaking, in a data-driven machine learning technique, a neural network is trained offline using time-resolved reflectance data generated by a Diffusion Equation model or by a Monte-Carlo multilayer model using known optical properties and geometrical properties in a multi-layer structure similar to the TFO structure to be measured. Note that as the experimental data from the measured reflectance curves 704 are obtained, they can be fed to trained neural network to obtain the optical properties of the tissues in real time. Generally speaking, the result from the machine learning technique can be more accurate and the online measurement does not require significant computational resources, thereby allowing real-time oxygen saturation data to be generated.

Figure 8:
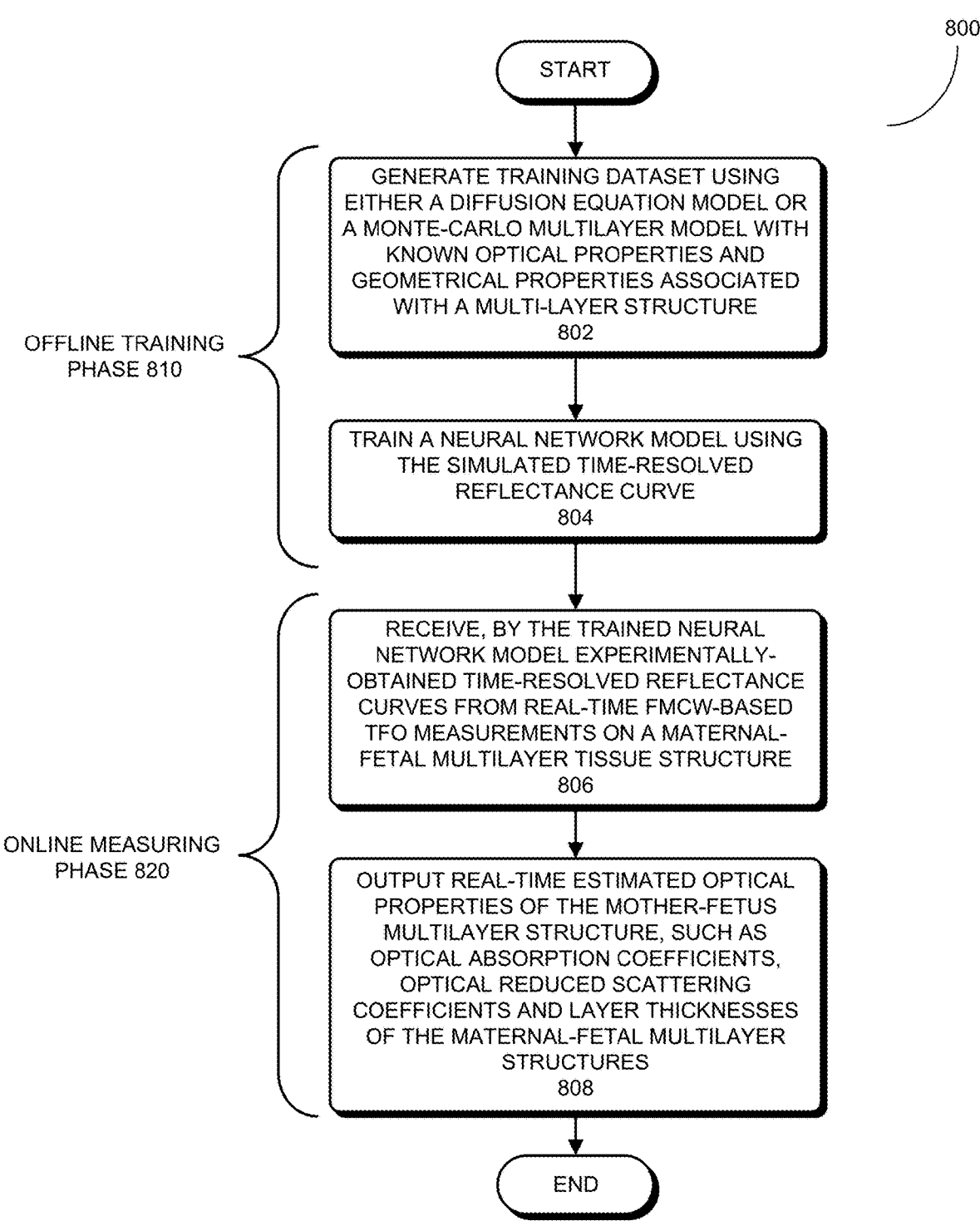
FIG. 8 presents a flowchart illustrating a data-driven machine learning-based process for extracting the optical properties of the measured tissues from the measured time-resolved reflectance generated by the disclosed FMCW time-domain spectroscopy in accordance with the disclosed embodiments.

FIG. 8 presents a flowchart illustrating a data-driven machine learning-based process 800 for extracting the optical properties of the measured tissues from the measured time-resolved reflectance generated by a disclosed FMCW time-domain spectroscopy in accordance with the disclosed embodiments. Note that the machine-learning-based process 800 is composed of an offline training phase 810 followed by an online measuring phase 820. Process 800 starts with offline training phase 810, which itself starts with generating training dataset using either a Diffusion Equation model or a Monte-Carlo multilayer model with known optical properties and geometrical properties associated with a multi-layer structure similar to a TFO structure to be measured (step 802). Note that the known optical properties and geometrical properties used to by the Diffusion Equation model or by the Monte-Carlo multilayer model can include: $\mu_{ai,\lambda j}$: absorption coefficient of the $i^{th}$ layer and $j^{th}$ wavelength; $\mu'_{si,\lambda j}$: reduced scattering coefficient of the $i^{th}$ layer and $j^{th}$ wavelength; $l_i$: thickness of $i^{th}$ layer in the multi-layer structure; $SD_k$: source-detector distance of $k^{th}$ detector, wherein i=1, . . . , N, in a N-layer tissue structure, j=1, . . . , M, for M light sources used; and k=1, . . . , P, for P detectors used. Note that the generated training dataset includes simulated time-resolved reflectance curve for the multi-layer structure.

Next in offline training phase 810, process 800 trains a neural network model, such as a convolutional neural network (CNN) model or a recurrent neural network (RNN)

model, using the simulated time-resolved reflectance curve (step 804). Note that the training neural network model can be used to predict optical absorption coefficients, optical reduced scattering coefficients and the layer thicknesses of other multi-layer structures. After step 804, offline training phase 810 ends and online measuring phase 820 can begin.

Specifically, online measuring phase 820 of process 800 begins with receiving, by the trained neural network model, experimentally-obtained time-resolved reflectance curves from real-time FMCW-based TFO measurements on a maternal-fetal multilayer tissue structure (step 806). Next, the trained neural network model outputs real-time estimated optical properties of the maternal-fetal multilayer tissue structure, such as optical absorption coefficients, optical reduced scattering coefficients and layer thicknesses of the maternal-fetal multi-layer structures (step 808). Note that when two or more laser wavelengths are used, the trained neural network model can also output absolute concentrations of the oxygenated hemoglobin and deoxygenated hemoglobin for mother and fetus, which can be used to compute oxygen saturation levels for both the mother and fetus based on Eqn. (4). In some embodiments, the real-time optical properties generated by the trained neural network model can be used as additional training data to refine the current trained neural network model.

Figure 9:
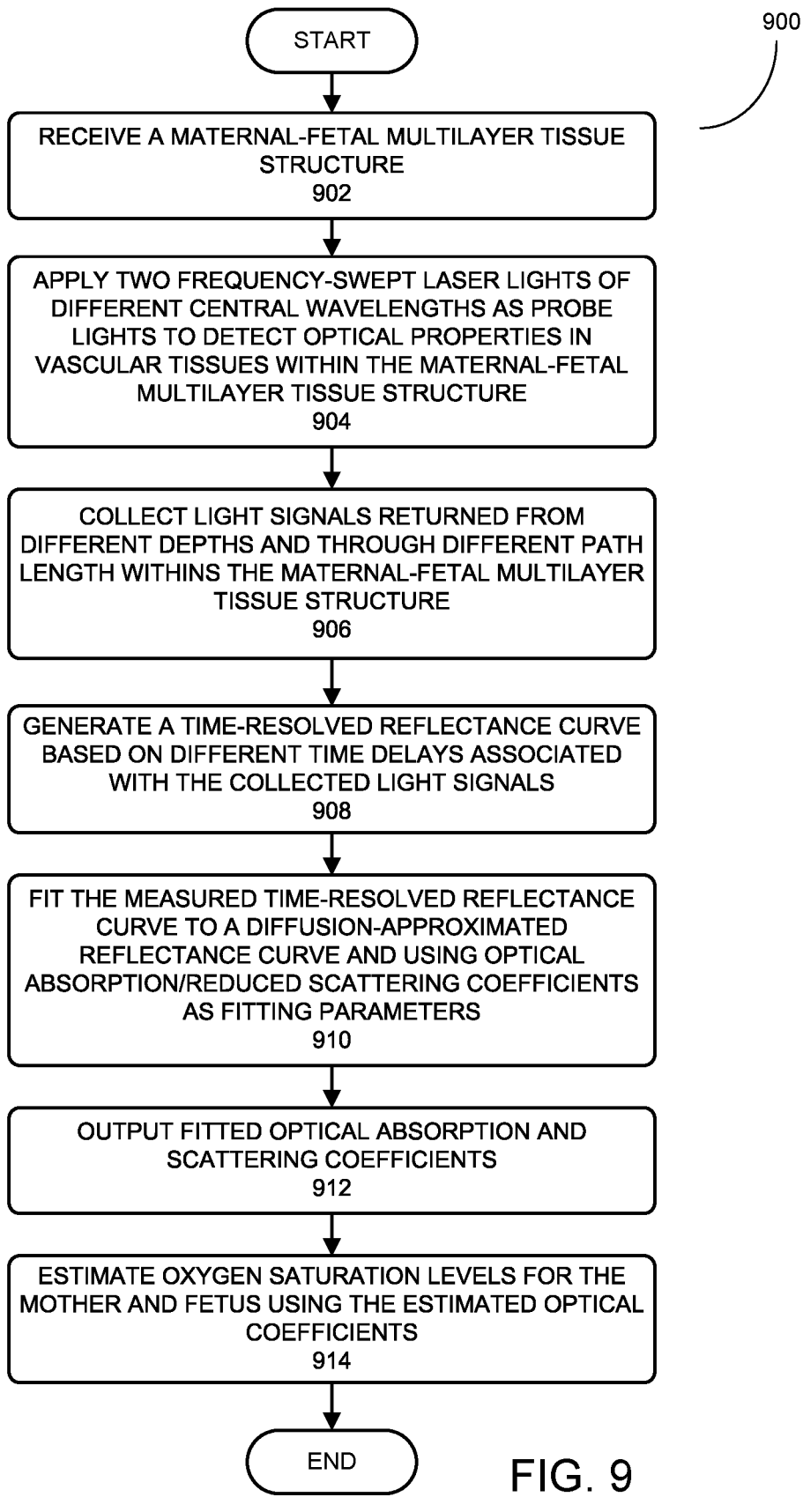
FIG. 9 presents a high-level flowchart illustrating a process performed by the disclosed FMCW-based TFO system to obtain accurate estimates of fetal oxygen saturation levels, in accordance with the disclosed embodiments.

FIG. 9 presents a high-level flowchart illustrating a process 900 performed by a disclosed FMCW-based TFO system to obtain accurate estimates of fetal oxygen saturation levels in accordance with the disclosed embodiments.

Process 900 may begin by receiving a maternal-fetal multilayer tissue structure (step 902). Next, process 900 applies two frequency-swept laser lights of different central wavelengths as probe lights to detect optical properties in vascular tissues within the maternal-fetal multilayer tissue structure (step 904). Process 900 then collects light signals returned from different depths and through different TOFs/path-lengths within the maternal-fetal multilayer tissue structure (step 906). In some embodiments, process 900 collects returned light signals using two or more detectors placed at multiple locations on the surface of the maternal-fetal multilayer tissue structure based on the predicted two or more peak-intensity return signal locations. Process 900 subsequently generates a time-resolved reflectance curve based on different time delays associated with the collected light signals (step 908). However, as described below, process 900 can also collect returned light signals using a single detectors placed at a single location on the surface of the maternal-fetal multilayer tissue structure.

Next, process 900 fits the measured time-resolved reflectance curve to a diffusion-approximated reflectance curve generated by a multilayer diffusion model and using optical absorption/reduced scattering coefficients as fitting parameters (step 910). In some embodiments, process 900 performs the model fitting by using a nonlinear fitting through an iterative optimization process described above in conjunction with FIG. 7. In other embodiments, instead of performing curve-model fitting, process 900 performs a data-driven machine-learning based on a training neural network model trained to predict optical absorption coefficients, optical reduced scattering coefficients and the layer thicknesses in the multi-layer structure. This machine learning approached has been described in conjunction with FIG. 8. Next, process 900 outputs fitted optical absorption and reduced scattering coefficients (step 912). Finally, process 900 estimates oxygen saturation levels for the mother and fetus using the estimated optical absorption and scattering coefficients and Eqns. (1) and (4) in this disclosure (step 914).

FIG. 10 presents a flowchart illustrating a process 1000 performed by the disclosed FMCW near-infrared spectroscopy to generate a time-resolved reflectance curve from the collected optical signals having different time delays in accordance with the disclosed embodiments.

Process 1000 begins by using a first wavelength swept light source to generate a first probe light having a center wavelength of $\lambda_1$ and a second wavelength swept light source to generate a second probe light having a center wavelength of $\lambda_2$ (step 1002). In various embodiments, the two wavelengths of the two light sources are continuously and periodically swept based on a linear waveform, such as a sawtooth waveform.

Next, process 1000 combines the two probe lights based on a specific multiplexing scheme so that the two signals do not interfere with each other during the entire TFO process (step 1004). Next, the combined probe light is split into (1) a reference light, which is guided into a reference arm, and (2) a sample light, which is guided onto a first location on the maternal abdomen of the maternal-fetal multilayer tissue structure (step 1006). Note that a portion of the sample light in the sample arm penetrates through both a maternal tissue layer and an underlining fetal tissue layer, and the diffused/scattered and reflected light forms a band of time-delayed optical signals that is collected at a second location on the maternal abdomen surface (step 1008). Next, process 1000 mixes the collected optical signals from the fetus with the reference light to effectuate interference between the collected optical signals and the reference light (step 1010). Process 1000 subsequently receives two non-overlapping bands of beat frequencies associated with the two light sources (step 1012). Note that the separation between the two bands can be achieved using different frequency sweeping rates at the source or adding additional delay for one of the two probe lights in one of the reference arms. Process 1000 next generates a time-resolved frequency spectrum for the two non-overlapping bands of beat frequencies (step 1014). Finally, process 1000 performs an inverse Fourier Transformation to convert the frequency spectrum into a time-resolved reflectance curve (step 1016).

FMCW Spectroscopy and FMCW-Based TFO with More Probe Lights

Note that in the embodiments of FMCW-based TFO systems 300-600 and the corresponding FMCW time-domain spectroscopy in conjunction with FIGS. 3-6, two light sources at two central wavelengths $\lambda_1$ and A are used to generate two probe lights. However, other embodiments of the disclosed FMCW time-domain spectroscopy and disclosed FMCW-based TFO system can use one or more additional frequency-modulated light sources in the same manner as the first two light sources to provide additional probe light. For example, the disclosed FMCW time-domain spectroscopy and disclosed FMCW-based TFO system can use a third frequency-modulated light source to generate a third probe light having a central wavelength of $\lambda_3$. This third probe light is concurrently used with the first and second probe lights through the same FMCW-based TFO measurement steps. Note that by adding one or more additional probe lights in the disclosed FMCW time-domain spectroscopy and the disclosed FMCW-based TFO system for FMCW-based measurements, the fetal blood oxygenation level measurement accuracies can generally be increased.

Single Detector FMCW Spectroscopy and FMCW-Based TFO

Note that in the embodiments of FMCW-based TFO systems 300-600 and the corresponding FMCW time-domain spectroscopy in conjunction with FIGS. 3-6, two detectors D1 and D2 placed at different distances SD1 and SD2 from the corresponding probes 320, 420, 520, 620 are used to separately collect the returned optical signals primarily from the maternal tissues (also referred to as the "maternal signals"), and returned optical signals that traversed the entire maternal-fetal multilayer tissue structure (also referred to as the "mixed maternal-fetal signals" or simply the "mixed signals"). However, other embodiments of the disclosed FMCW time-domain spectroscopy and disclosed FMCW-based TFO system can be implemented by using a single detector D in place of D1 and D2 to collect both the maternal signals and the mixed maternal-fetal signals. For example, this single detector D may be placed at a distance SD3 (SD2>SD3>SD1) on the maternal abdomen surface somewhere between D1 and D2 (e.g., approximately halfway between D1 and D2) in each of the FMCW-based TFO systems 300-600 to replace D1 and D2.

Note that the maternal signals and the mixed maternal-fetal signals (such as signals 316 and 318, signals 416 and 418, signals 516 and 518, and signals 616 and 618) are distinctly different in their corresponding time-of-flights (TOFs), and therefore are inherently well-separated in the time-domain. In the embodiments of using a single detector D, the corresponding FMCW spectroscopy and FMCW-based TFO system generates a combined time-resolved reflectance curve for the optical signals collected by detector D that includes both the maternal signals and the mixed maternal-fetal signals. Because the disclosed FMCW time-domain spectroscopy can generate a time-resolved reflectance curve that separates/resolves in the time-domain the detected optical signals having different TOFs/path-lengths for each band of the maternal signals and the mixed maternal-fetal signals, this combined time-resolved reflectance curve separates the two bands of returned signals: the maternal signals and the mixed maternal-fetal signals in the time-domain into two substantially non-overlapping portions of the resolved reflectance curve. Moreover, and in the same manner described above, in each portion of the combined time-resolved reflectance curve corresponding to a respective band of signals, the optical signals having different TOFs/path-lengths are also separated and resolved in the time-domain as individual reflectance vs. time delay points.

Figure 11A:
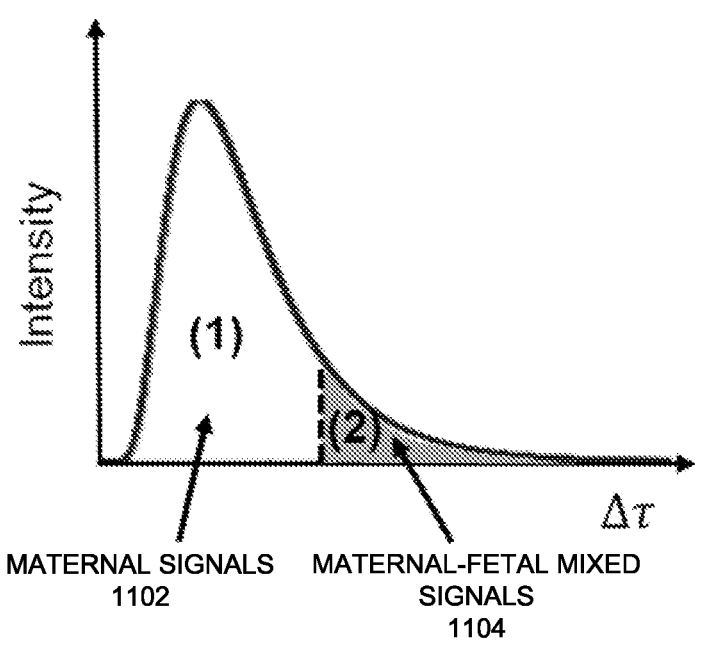
FIG. 11A shows an exemplary combined time-resolved reflectance curve generated by a disclosed FMCW time-domain spectroscopy that uses a single detector on the maternal abdomen to collect both the maternal signals and the mixed maternal-fetal signals, in accordance with the disclosed embodiments in accordance with the disclosed embodiments.

FIG. 11A shows an exemplary combined time-resolved reflectance curve 1100 generated by a disclosed FMCW time-domain spectroscopy that uses a single detector on the maternal abdomen to collect both the maternal signals and the mixed maternal-fetal signals, in accordance with the disclosed embodiments. As can be seen in FIG. 11A, area (1) (the early portion of the combined time-resolved reflectance curve 1100) corresponds to time-resolved maternal signals 1102 (e.g., those signals 316, signals 416, signals 516 and signals 616 in FIGS. 3-6), which mostly captures the photons from the maternal tissues ($(L_{fet})s \approx 0$). The area under the early portion of the combined time-resolved reflectance curve 1100 represents the intensity of the light signals after traversing the shallow tissues in the maternal tissues.

Separately, area (2), or the tail portion of the combined time-resolved reflectance curve 1100, corresponds to time-resolved mixed maternal-fetal signals 1104 (e.g., those signals 318, signals 418, signals 518 and signals 618 in FIGS. 3-6), which captures both maternal and fetal information. The area under the tail portion of the combined time-resolved reflectance curve 1100 represents the intensity of the light signals after traversing the deep tissues (including both maternal tissues and fetal tissues). Note that maternal signals 1102 generally have significantly higher intensities than mixed maternal-fetal signals 1104 because they are generated at much shallower depths of the maternal-fetal multilayer structure. Time-resolved reflectance curve 1100 can be fed to a processing unit (e.g., any of units 360, 460, 560, 660) so that the fetal oxygen saturation level can be extracted.

FMCW Pulse Oximetry

Measurements in the conventional CW fetal pulse oximetry rely on the fetal pulsations (therefore referred to as such), and the measurements need to be conducted continuously on the subject for a time duration of at least one heartbeat cycle (0.5~1 sec) in order to extract the oxygen saturation level. In practice, CW fetal pulse oximetry continuously measures many heartbeat cycles in time. However, the disclosed FMCW-based TFO does not need to rely on fetal pulsations. In principle, the FMCW-based TFO can determine one value of the fetal oxygen saturation level by measuring the subject during a single cycle of the laser sweeping. For example, if the frequency-sweeping rate is 1 kHz, then the measurement duration will be 1 ms. In practice, the FMCW-based TFO continuously measures many laser frequency-sweeping cycles. This allows the FMCW-based TFO to measure a sequence of values for the fetal oxygen saturation level. The sequence of values of the fetal oxygen saturation level can be used to compute average values to increase the measured signal accuracy, reduce noise level, and improve other signal qualities. Alternatively, the sequence of values of the fetal oxygen saturation level can be used to monitor the change of the fetal tissues at the measurement resolution determined by the source frequency sweeping rate.

Based on the different time scales described above for CW fetal pulse oximetry and the FMCW-based TFO, a person skilled in the art can appreciate that to be able to use the disclosed FMCW-based TFO for fetal pulse oximetry measurements, the measurements need to be continuously performed for many cycles of the source frequency sweeping, so that the combined measurement time becomes equivalent to the duration of one cycle of heart beat. In other words, the time-resolved reflectance curves are continuously measured for a time-duration throughout a give diastole-systole cycle (i.e., one cardiac cycle). In practice, FMCW-Based TFO measurements are continuously performed for a duration of more than one cycle of heart beat; in other words, the time-resolved reflectance curves are continuously measured for a time duration throughout many diastole-systole cycles (i.e., many cardiac cycles). This increases the measured signal accuracy, reduces noise level, and improves other signal qualities.

Figure 11B:
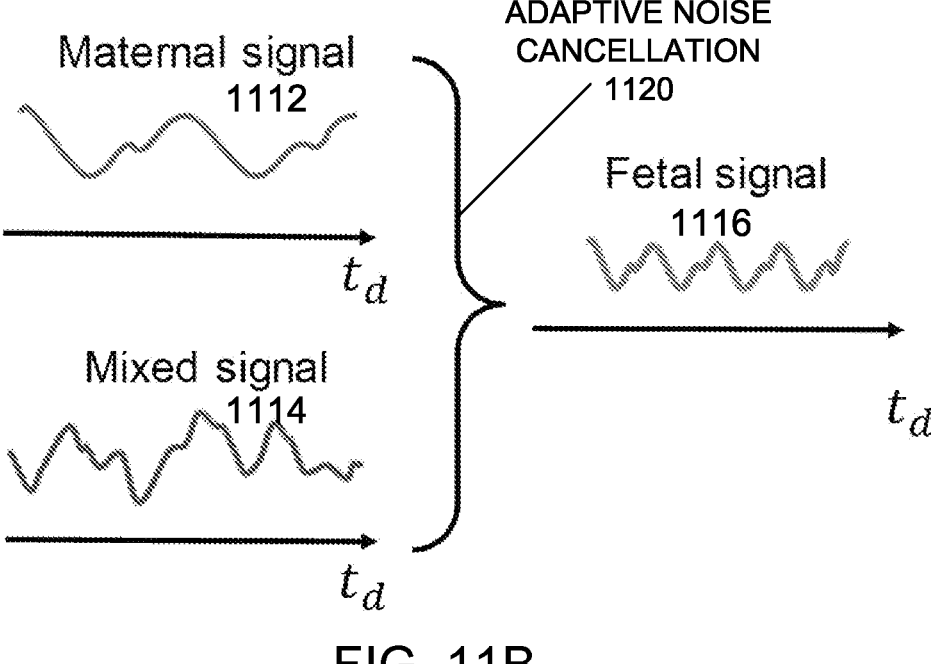
FIG. 11B illustrates an process of processing the combined time-resolved reflectance curve to extract the fetal signals during each source wavelength sweeping cycle, in accordance with the disclosed embodiments in accordance with the disclosed embodiments.

As described above, a single detector can be used to perform FMCW spectroscopy and FMCW-Based TFO. Each combined time-resolved reflectance curve represents a single measurement of the maternal-fetal multilayer structure for each probe-light wavelength sweeping cycle. In some embodiments, the combined time-resolved reflectance curves are continuously generated based on continuously measured maternal signals and mixed maternal-fetal signals corresponding to many source-wavelength-sweeping cycles. Note that these combined time-resolved reflectance curves can be used to extract the fetal signals. FIG. 11B illustrates a process of processing the combined time-resolved reflectance curve to extract the fetal signals during each source wavelength sweeping cycle.

As can be seen in FIG. 11B, combined time-resolved reflectance curve 1100 is segmented, and maternal signals 1102 from area (1) of the combined time-resolved reflectance curve 1100 are extracted and shown as maternal signals 1112. Mixed maternal-fetal signals 1104 from area (2) of the combined time-resolved reflectance curve 1100 are extracted and shown as mixed signals 1114. Next, fetal signals 1116 specific to the fetus can be extracted by "subtracting" maternal signals 1112 out of mixed signals 1114. In some embodiments, to "subtract" maternal signals 1112, an adaptive noise cancellation approach 1120 is used. Note that "noise" herein refers to maternal signals 1112, and the noise cancellation process achieves the effect of subtraction. This adaptive noise cancellation approach was described in "Design and In Vivo Evaluation of a Non-Invasive Transabdominal Fetal Pulse Oximeter," in IEEE TRANSACTIONS ON BIOMEDICAL ENGINEERING, VOL. 68, NO. 1, JANUARY 2021, pages 256-266. However, other machine-learning-based techniques may also be used to remove the effect of maternal tissues from the mixed maternal-fetal signals 1114 based on maternal signals 1112 and mixed signals 1114.

Note that for light traversing the shallow (S) and deep (D) tissues, the change in its attenuation ΔA between systole and diastole can be identified by Modified Beer-Lambert Law (dMBLL) and expressed as:

$$\Delta A_S = \log_{10} \frac{I_{systole,S}}{I_{diastole,S}} = \Delta \mu_{a,mat} * (L_{mat})_S, \quad (5)$$

for light traversing the shallow tissues, which correspond to maternal signals 1102; and $$\Delta A_D = \log_{10} \frac{I_{systole,D}}{I_{diastole,D}} = \Delta \mu_{a,mat} * (L_{mat})_D + \Delta \mu_{a,fet} * (L_{fet})_D \quad (6)$$

for light traversing the deep tissues, which correspond to the mixed maternal and fetal signals 1104, wherein $\Delta\mu_{\alpha,mat}$ and $\Delta\mu_{\alpha,fet}$ are the absorption coefficients for maternal and fetal tissues, respectively, and $\langle L_{mat} \rangle$ and $\langle L_{fet} \rangle$ are the expected photon path-lengths for maternal and fetal signals, accordingly. In some embodiments, the maternal signals within the mixed signals can be estimated based on maternal signals 1112 generated in the shallow (S) tissues. The fetal signals can be represented as:

$$\Delta A_{fet} = \Delta\mu_{afet} * \langle L_{fet}\rangle_D = \Delta A_D - \langle L_{mat}\rangle_D / \langle L_{mat}\rangle_S * \Delta A_S, \quad (7)$$

wherein $\langle L_{mat}\rangle_D / \langle L_{mat}\rangle_S$ is the ratio of the partial path-lengths coming through the maternal tissues from shallow and deep trajectory. Herein, we denote $\langle L_{mat}\rangle_D / \langle L_{mat}\rangle_S$ as α. Assuming the fetal signals are uncorrelated to the maternal signals, we can implement the adaptive noise cancellation technique mentioned above to extract the fetal signal by adjusting the adaptive filter (α) to reach the minimize error in an optimization process.

Figure 12:
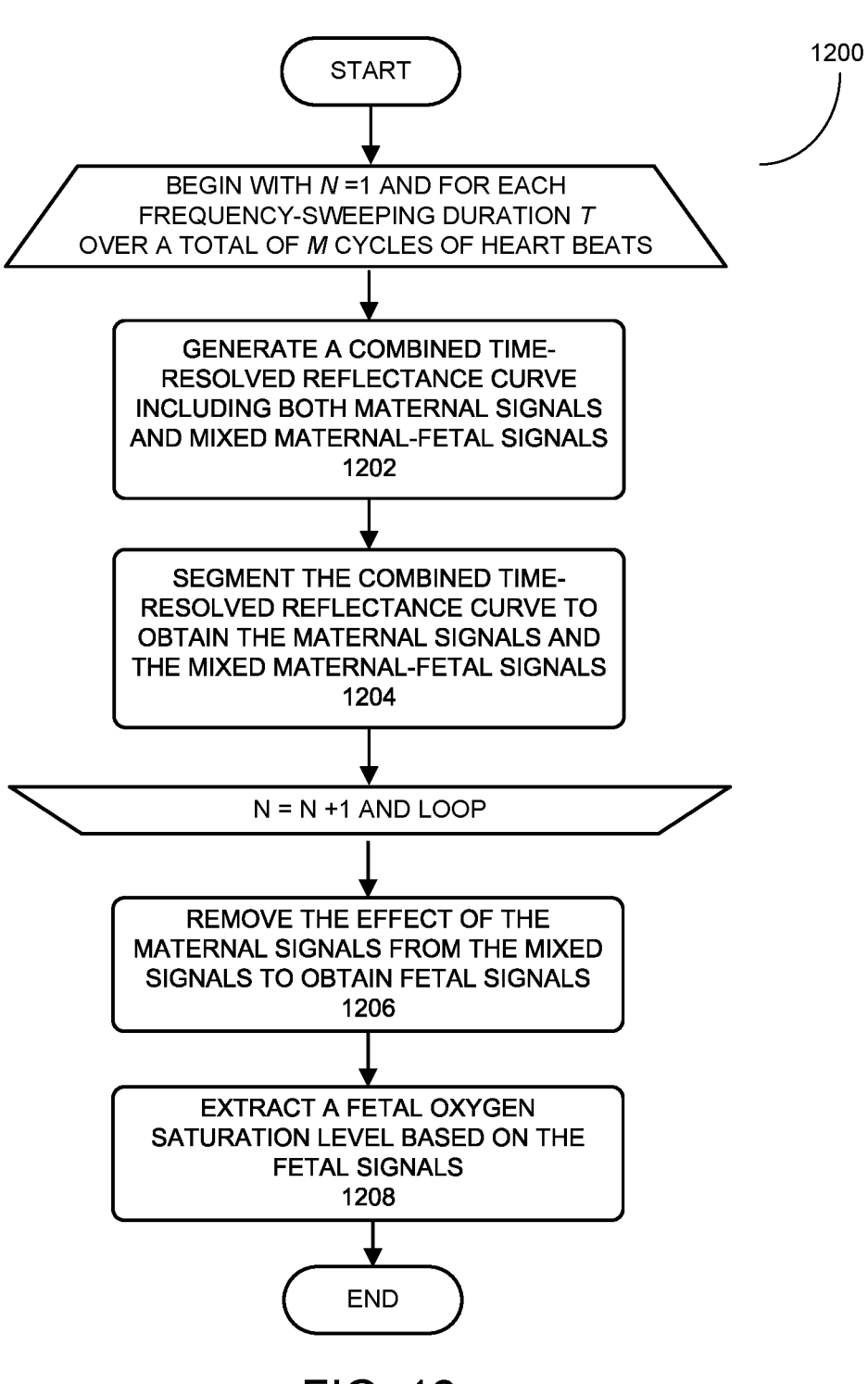
FIG. 12 presents a flowchart illustrating a process of performing a transabdominal fetal pulse oximetry using the disclosed FMCW near-infrared spectroscopy in accordance with the disclosed embodiments.

FIG. 12 presents a flowchart illustrating process 1200 for performing a transabdominal fetal pulse oximetry using the disclosed FMCW near-infrared spectroscopy, in accordance with the disclosed embodiments. Note that process 1200 is performed in a loop over a duration of M cycles of heart beat (typically $1 \leq M \leq 100$), wherein a fetal oxygen saturation level is continuously measured using the above-described single-detector FMCW-based TFO technique in each frequency-sweeping cycle of duration T, for a total of N cycles, wherein N×T=M cycles of heart beat.

Specifically, for each frequency-sweeping cycle T, process 1200 involves performance of a single-detector FMCW spectroscopy operation to generate a combined time-resolved reflectance curve that includes both the maternal signals and the mixed maternal-fetal signals (step 1202). Next, the combined time-resolved reflectance curve is segmented to separately obtain the maternal signals and the mixed maternal-fetal signals from the combined time-resolved reflectance curve based on the above-described segmentation techniques (step 1204).

The illustrated process then loops for the next frequency-sweeping cycle T. When the total duration reaches one or more cycles of heart beat, the maternal signals over a time duration of one or more cycles of heart beat (i.e. 1112), and the mixed maternal-fetal signals over a time duration of one or more cycles of heart beat (i.e. 1114) have been collected. Effects of the maternal signals are then removed from the mixed maternal-fetal signals to obtain the fetal signals 1116 (step 1206). For example, the adaptive noise cancellation approach described above can be performed to remove the maternal-signal effect. Fetal oxygen saturation level SpO$_2$ is subsequently extracted from the fetal signal (step 1208). At this point, the illustrated method either terminates or returns to the beginning of the loop to perform the next fetal pulse oximetry measurement.

Hybrid FMCW-CW Transabdominal Fetal Pulse Oximetry

In the discussion above regarding the two-wavelength CW transabdominal fetal pulse techniques, we note that even when two light sources are used, the CW technique is unable to measure the expected photon path-lengths $\langle L \rangle_{\lambda 1}$ and $\langle L \rangle_{\lambda 2}$, or the ratio of the two expected photon path-lengths $\langle L \rangle_{\lambda 1} / \langle L \rangle_{\lambda 2}$. However, we have shown that the disclosed two-wavelength FMCW time-domain spectroscopy can extract the optical path-lengths $\langle L \rangle_{\lambda 1}$ and $\langle L \rangle_{\lambda 2}$ passing through both the mother and fetus based on the determined time resolved reflectance. Further, notice that the measurement setup for the two-wavelength CW transabdominal fetal pulse techniques and the disclosed two-wavelength FMCW time-domain spectroscopy differ regarding whether the light sources are frequency modulated or constant. In addition, the two-wavelength CW transabdominal fetal pulse techniques are not configured as an interferometer.

Hence, a hybrid FMCW-CW transabdominal fetal pulse oximetry is proposed, wherein each of the two lasers can be switched between two operation modes: the two-wavelength CW transabdominal fetal pulse mode and the disclosed FMCW time-domain spectroscopy mode. More specifically, the proposed hybrid FMCW-CW transabdominal fetal pulse oximetry has a common measurement setup but two modes of operations. To measure the fetal oxygen saturation level, the hybrid FMCW-CW transabdominal fetal pulse oximetry is first set up as a FMCW time-domain spectroscopy by enabling frequency modulations on the two tunable laser sources. Moreover, the FMCW time-domain spectroscopy is implemented as an optical interferometer as described before. Next, the optical path-lengths passing through both the mother and fetus for both wavelengths $\lambda_1$ and $\lambda_Z$ of the two laser are obtained based on the determined time resolved reflectance values.

Once the necessary optical path-lengths are determined, the hybrid FMCW-CW transabdominal fetal pulse oximetry is switched to the two-wavelength CW transabdominal fetal pulse mode by simply disabling the frequency modulations on the two tunable laser sources. Under the two-laser CW operation mode, continuous-wave near infrared spectroscopy can be performed. Using the optical path length data obtained in the FMCW mode, the oxygen saturation $SpO_2$ can be accurately extracted for both the mother and fetus by using the techniques that separate the maternal and fetal signals and the Modified Beer-Lambert law model. Note that approximations such as assuming the ratio of two pathlength factors $B_{\lambda 1}/B_{\lambda 2} \approx 1$ are no long required.

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A frequency-modulated continuous-wave (FMCW) method for non-invasively measuring a fetal blood oxygenation level, the method comprising:

receiving a first frequency-modulated light source having a central wavelength of $\lambda_1$ as a first probe light;

receiving a second frequency-modulated laser source having a central wavelength of $\lambda_2$ as a second probe light;

splitting the first probe light into a first reference light and a first sample light and the second probe light into a second reference light and a second sample light;

using the first probe light and the second probe light to probe a maternal-fetal multilayer tissue structure, thereby generating a first band of light signals and a second band of light signals carrying information of the maternal-fetal multilayer tissue structure;

mixing the first and second reference lights with the first and second bands of light signals, respectively, to effectuate interference between the first or the second reference light and the first or second band of light signals to produce a band of beat frequencies;

generating a time-resolved reflectance curve based on the band of beat frequencies;

determining a set of optical properties for the fetus in the maternal-fetal multilayer tissue structure for both central wavelengths $\lambda_1$ and $\lambda_2$; and performing a pulse-oximetry computation based on the determined optical properties to determine a fetal oxygen saturation level.

2. The FMCW method of claim 1, wherein each of the first and second reference lights propagates a known distance toward a coupler while each of the first and second sample lights propagates a first distance incident to a maternal abdomen of the maternal-fetal multilayer tissue structure, wherein each of the sample lights traverses the maternal abdomen and is scattered inside the fetus into the first or the second band of light signals of a range of optical path lengths, and wherein the first and second bands of light signals propagate back to a surface of the maternal abdomen and are collected by one or more detectors.

3. The FMCW method of claim 2, wherein each of the first and second band of light signals propagates a second distance from the one or more detectors toward a coupler, wherein the sum of the first distance and the second distance is substantially equal to the known distance.

4. The FMCW method of claim 1, wherein a time-resolution of the time-resolved reflectance curve is increased by increasing a frequency-sweeping range of the first and the second frequency-modulated light sources.

5. The FMCW method of claim 1, wherein the generated time-resolved reflectance curve comprises a first portion of the time-resolved reflectance curve corresponding to the first probe light with central wavelengths $\lambda_1$ and a second portion of the time-resolved reflectance curve corresponding to the second probe light with central wavelengths $\lambda_2$.

6. The FMCW method of claim 1, wherein the wavelengths/frequencies of the first and the second frequency-modulated light sources are continuously and periodically modulated based on a wavelength/frequency modulation waveform.

7. The FMCW method of claim 6, wherein the wavelength/frequency modulation waveform is either a linear waveform or a nonlinear waveform.

8. The FMCW method of claim 6, wherein the maximum range of wavelength modulation of the first and the second frequency-modulated light sources is significantly smaller than the difference between $\lambda_1$ and $\lambda_2$.

9. The FMCW method of claim 1, wherein generating the time-resolved reflectance curve based on the band of beat frequencies includes:

generating a beat spectrum based on the band of beat frequencies and a corresponding set of intensity values of the band of beat frequencies; and obtaining the time-resolved reflectance curve by performing an inverse Fourier Transformation (iFT) on the beat spectrum.

10. The FMCW method of claim 1, wherein each data point on the time-resolved reflectance curve specifies both a reflectance value and a time-delay of a given light signal in either the first or the second band of light signals.

11. The FMCW method of claim 1, wherein the time-resolved reflectance curve has a bell-shaped distribution.

12. The FMCW method of claim 1, wherein the time-resolved reflectance curve includes two non-overlapping bell-shaped distributions that correspond to the first probe light and the second probe light, respectively.

13. The FMCW method of claim 1, wherein:

the time-resolved reflectance curve is regenerated for each frequency modulation period of the first probe light and the second probe light; and each regenerated time-resolved reflectance curve is used to determine a new value of the fetal oxygen saturation level.

14. The FMCW method of claim 1, wherein the set of optical properties includes at least:

$\lambda_{\alpha,\lambda 1}$: a first optical absorption coefficient of fetal tissues in the maternal-fetal multilayer tissue structure corresponding to wavelengths $\lambda_1$; and $\lambda_{\alpha,\lambda 2}$: a second optical absorption coefficient of the fetal tissues in the maternal-fetal multilayer tissue structure corresponding to wavelengths $\lambda_2$.

15. The FMCW method of claim 14, wherein performing the oximetry computation based on the determined optical properties to determine a fetal oxygen saturation level includes:

extracting absolute concentrations of the oxygenated hemoglobin ($[HbO_2]$) and deoxygenated hemoglobin ($[Hb]$) associated with the fetal tissues using $\lambda_{\alpha,\lambda 1}$ and $\lambda_{\alpha,\lambda 2}$; and determining a new fetal oxygen saturation level by computing:

$$[HbO_2]/([HbO_2] + [Hb]) \times 100\%.$$

16. The FMCW method of claim 14, wherein the set of optical properties additionally includes:

a first optical reduced scattering coefficient of the fetal tissues corresponding to wavelengths $\lambda_1$; and a second optical reduced scattering coefficient of the fetal tissues corresponding to wavelengths $\lambda_2$.

17. The FMCW method of claim 1, wherein:

determining the set of optical properties for the fetus includes fitting the time-resolved reflectance curve to a multilayer tissue model for the maternal-fetal multilayer tissue structure;

fitting the time-resolved reflectance curve to the tissue model additionally produces absorption coefficients and/or reduced scattering coefficients for maternal tissues in the maternal-fetal multilayer tissue structure; and the oximetry computation additionally determines a maternal blood oxygenation level.

18. The FMCW method of claim 1, wherein collecting the first and second bands of light signals from the surface of the maternal abdomen comprises using a coupling technique selected from the group consisting of:

a fiber-based coupling technique;

a free-space-based coupling technique; and a hybrid fiber-based and free-space-based coupling technique.

19. The FMCW method of claim 1, wherein prior to splitting each of the first probe light and the second probe light into a reference light and a sample light, the method further comprises performing a multiplexing operation on the first probe light and the second probe light to combine the two probe lights by using a multiplexing technique selected from the group consisting of:

time-division multiplexing;

frequency-division multiplexing; and radio-frequency-division multiplexing.

20. The FMCW method of claim 1, wherein determining the set of optical properties based on the generated time-resolved reflectance curve comprises:

receiving a training neural network model which was trained based on a simulated time-resolved reflectance curve generated by a multilayer model that simulates the maternal-fetal multilayer tissue structure; and using the generated time-resolved reflectance as input to the trained neural network model, wherein the trained neural network model outputs estimated optical properties of the maternal-fetal multilayer tissue structure.

21. The FMCW method of claim 1, further comprising:

adding a third frequency-modulated light source to generate a third probe light having a central wavelength of $\lambda_3$; and applying the same processing steps of claim 1 on the third probe light while concurrently applying the same processing steps on the first and second probe light, wherein adding the third probe light in the process of measuring the fetal blood oxygenation level increases estimation accuracy of the FMCW method.

22. A frequency-modulated continuous-wave (FMCW) time-domain near-infrared spectroscopy system, the system comprising:

a first frequency-modulated light source to generate a first probe light having a central wavelength of $\lambda_1$;

a second frequency-modulated laser source to generate a second probe light having a central wavelength of $\lambda_2$;

an interferometer configured to determine a time-resolved reflectance curve for each of the first probe light and the second probe light during a fetal oximetry, wherein the interferometer further comprises:

a splitter configured to split the first probe light into a first reference light and a first sample light and the second probe light into a second reference light and a second sample light;

a guiding mechanism configured to guide the first probe light and the second probe light to probe a maternal-fetal multilayer tissue structure, thereby generating a first band of light signals and a second band of light signals carrying information of the maternal-fetal multilayer tissue structure; and a coupler configured to receive and mix the first and second reference lights with the first and second bands of light signals, respectively to effectuate an interference between the first or the second reference light and the first or second band of light signals to produce a band of beat frequencies; and a processing unit configured to generate a time-resolved reflectance curve based on the band of beat frequencies.

23. The FMCW time-domain near-infrared spectroscopy system of claim 22, wherein the guiding mechanism further comprises:

a reference arm having a known distance and configured to guide the first and the second reference lights toward the coupler; and a sample arm configured to guide the first and second sample lights to incident on a maternal abdomen of the maternal-fetal multilayer tissue structure, wherein each of the sample lights traverses through the maternal abdomen and is scattered inside the fetus into the first or the second band of light signals of a range of optical path lengths, and wherein the first and second bands of light signals propagate back onto a surface of the maternal abdomen and collected by one or more detectors.

24. The FMCW time-domain near-infrared spectroscopy system of claim 23, wherein the one or more detectors are configured to couple the first and second bands of light signals from the surface of the maternal abdomen to the coupler through a second distance, wherein the sum of the first distance and the second distance is substantially equal to the known distance.

25. The FMCW time-domain near-infrared spectroscopy system of claim 22, further comprising a wavelength/frequency modulation module configured to continuously and periodically modulate the first probe light and the second probe light based on a wavelength/frequency modulation waveform.

26. The FMCW time-domain near-infrared spectroscopy system of claim 22, wherein the processing unit is configured to generate a time-resolved reflectance curve by:

generating a beat spectrum based on the band of beat frequencies and a corresponding set of intensity values of the band of beat frequencies; and obtaining the time-resolved reflectance curve by performing an inverse Fourier Transformation (iFT) on the beat spectrum.

27. The FMCW time-domain near-infrared spectroscopy system of claim 22, wherein the processing unit is further configured to:

regenerate a new time-resolved reflectance curve for each frequency modulation period of the first probe light and the second probe light, wherein each regenerated time-resolved reflectance curve is used to determine a new value for a fetal blood oxygenation level.

28. The FMCW time-domain near-infrared spectroscopy of claim 22, wherein the processing unit is further configured to:

determine a set of optical properties for the fetus in the maternal-fetal multilayer tissue structure for both central wavelengths $\lambda_1$ and $\lambda_2$ by fitting the time-resolved reflectance curve to a multilayer tissue model for maternal tissues and fetal tissues; and perform an oximetry computation based on the determined optical properties to determine a fetal blood oxygenation level.

29. The FMCW time-domain near-infrared spectroscopy system of claim 22, further comprising a multiplexer (MUX) positioned before the splitter and configured to perform a multiplexing operation on the first probe light and the second probe light to combine the two probe lights by using a multiplexing technique selected from the group consisting of:

time-division multiplexing;

frequency-division multiplexing; and radio-frequency-division multiplexing.

30. The FMCW time-domain near-infrared spectroscopy system of claim 22, further comprising a third frequency-modulated light source to generate a third probe light having a central wavelength of $\lambda_3$; and wherein the interferometer is further configured to determine the time-resolved reflectance curve for the third probe light during the fetal pulse-oximetry.

31. A frequency-modulated continuous-wave (FMCW) method for non-invasively measuring a fetal blood oxygenation level, comprising:

using a first wavelength swept laser source to generate light having a central wavelength $\lambda_1$;

using a second wavelength swept laser source to generate light having a central wavelength $\lambda_2$;

using an interferometer to determine a time-resolved reflectance for each of the two central wavelengths $\lambda_1$ and $\lambda_2$ by:

splitting light from the first and second swept laser sources between a reference arm that has a known distance, and a sample arm that directs light into a maternal abdomen of a pregnant mammal toward a fetus, and returns reflected light that is coupled from different detection locations on the maternal abdomen;

combining light from the reference and sample arms to produce time-domain interference fringe patterns; and calculating the time-resolved reflectances based on the time-domain interference fringe patterns;

determining absorption coefficients and/or reduced scattering coefficients for the fetal tissue for both central wavelengths $\lambda_1$ and $\lambda_2$ by fitting the time-resolved reflectances to a tissue model for maternal tissue and fetal tissue based on known source-to-detector distances; and performing a pulse-oximetry computation based on the determined absorption coefficients to determine the fetal blood oxygenation level.

* * * * *